(12) United States Patent
Shelton, IV et al.

(10) Patent No.: US 10,172,635 B2
(45) Date of Patent: Jan. 8, 2019

(54) SURGICAL DEVICES WITH ARTICULATING END EFFECTORS AND METHODS OF USING SURGICAL DEVICES WITH ARTICULATING END EFFECTORS

(71) Applicant: Ethicon Endo-Surgery, LLC, Guaynabo, PR (US)

(72) Inventors: Frederick E. Shelton, IV, Hillsboro, OH (US); Chester O. Baxter, III, Loveland, OH (US); Charles J. Scheib, Loveland, OH (US); Gregory W. Johnson, Milford, OH (US); John R. Dugan, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 210 days.

(21) Appl. No.: 15/391,304

(22) Filed: Dec. 27, 2016

(65) Prior Publication Data
US 2017/0172596 A1 Jun. 22, 2017

Related U.S. Application Data

(63) Continuation of application No. 14/230,027, filed on Mar. 31, 2014, now Pat. No. 9,549,750.

(51) Int. Cl.
*A61B 17/29* (2006.01)
*A61B 17/00* (2006.01)

(52) U.S. Cl.
CPC .......... *A61B 17/2909* (2013.01); *A61B 17/29* (2013.01); *A61B 2017/00398* (2013.01);
(Continued)

(58) Field of Classification Search
CPC ................ A61B 17/29; A61B 17/2909; A61B 2017/2903; A61B 2017/00398;
(Continued)

(56) References Cited

U.S. PATENT DOCUMENTS 5,626,607 A   5/1997   Malecki et al.
5,817,119 A   10/1998  Klieman et al.
(Continued)

FOREIGN PATENT DOCUMENTS

WO   WO-9102493 A1   3/1991
WO   WO-2014085390 A1   6/2014

OTHER PUBLICATIONS

International Search Report for PCT Application No. PCT/US2015/018632, dated May 11, 2015.

*Primary Examiner* — Son Dang
(74) *Attorney, Agent, or Firm* — Mintz Levin Cohn Ferris Glovsky and Popeo, P.C.

(57) ABSTRACT

Methods and devices for using surgical devices with articulating end effectors are provided. Surgical devices with articulating end effectors can provide rotary driven pivoting of the end effector. In some embodiments, the device can include a handle, a first and a second tube extending from the handle, the second tube disposed within the first tube, and an end effector that includes a pair of distal jaws configured to move in response to rotation of the first tube about a longitudinal axis thereof and rotation of the second tube about a longitudinal axis thereof. The jaws can move in two different ways depending on whether the first and second tubes are rotating in a same direction as one another or in different ways than each other. The jaws can open/close and articulate using the same mechanical mechanism. The device can be powered, or the device can be non-powered.

4 Claims, 22 Drawing Sheets

(52) U.S. Cl.
CPC . *A61B 2017/292* (2013.01); *A61B 2017/2903* (2013.01); *A61B 2017/2916* (2013.01); *A61B 2017/2919* (2013.01); *A61B 2017/2923* (2013.01); *A61B 2017/2927* (2013.01); *A61B 2017/2938* (2013.01); *A61B 2017/2943* (2013.01)

(58) Field of Classification Search
CPC .... A61B 2017/2927; A61B 2017/2919; A61B 2017/2923; A61B 2017/2943; A61B 2017/2938; A61B 2017/2916; A61B 2017/292
See application file for complete search history.

(56) References Cited

U.S. PATENT DOCUMENTS

| | | |
|---|---|---|
| 9,549,750 B2 | 1/2017 | Shelton et al. |
| 2002/0040217 A1 | 4/2002 | Jinno |
| 2004/0122423 A1 | 6/2004 | Dycus et al. |
| 2006/0219065 A1 | 10/2006 | Jinno et al. |
| 2009/0088750 A1 | 4/2009 | Hushka et al. |
| 2009/0182327 A1 | 7/2009 | Unger |

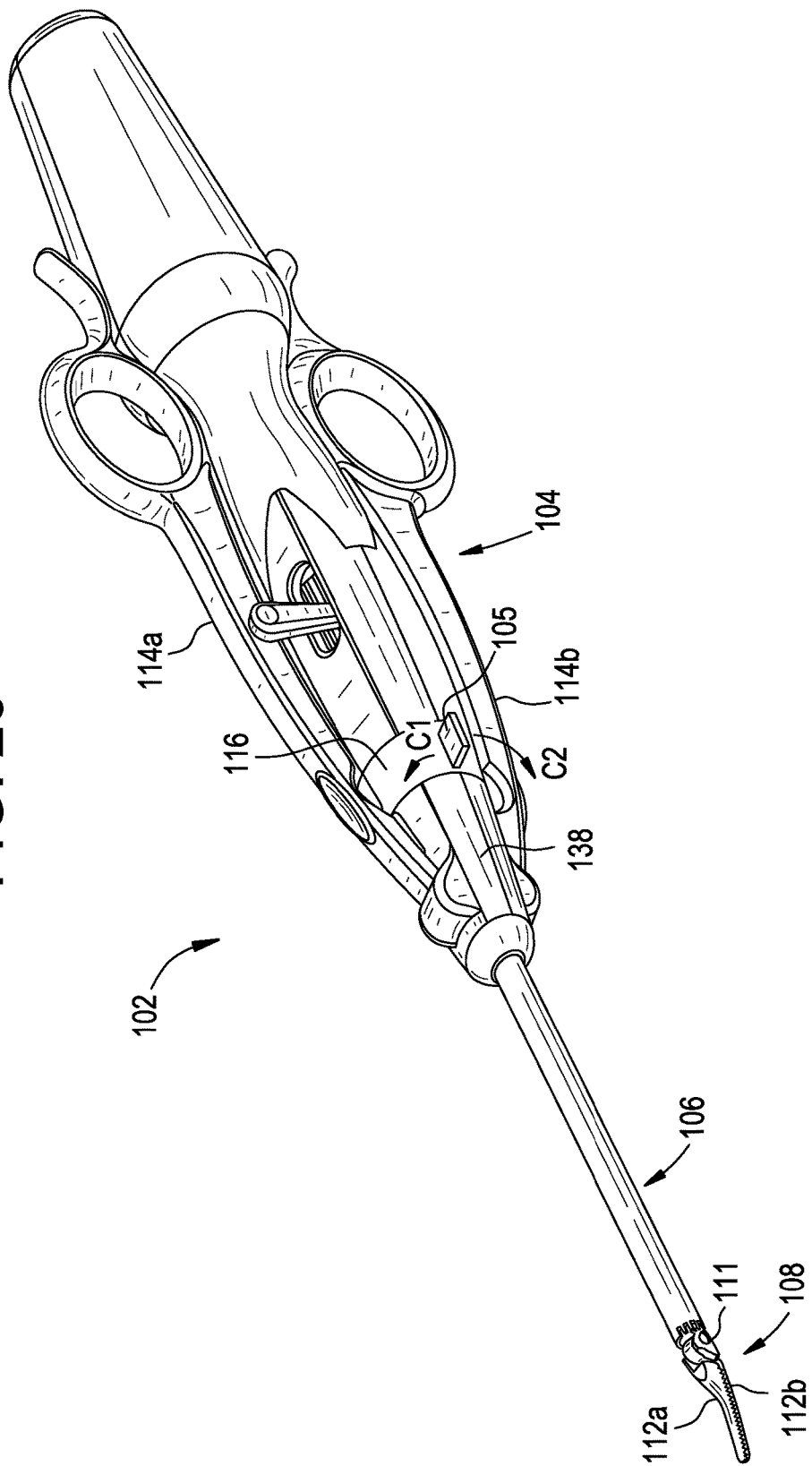

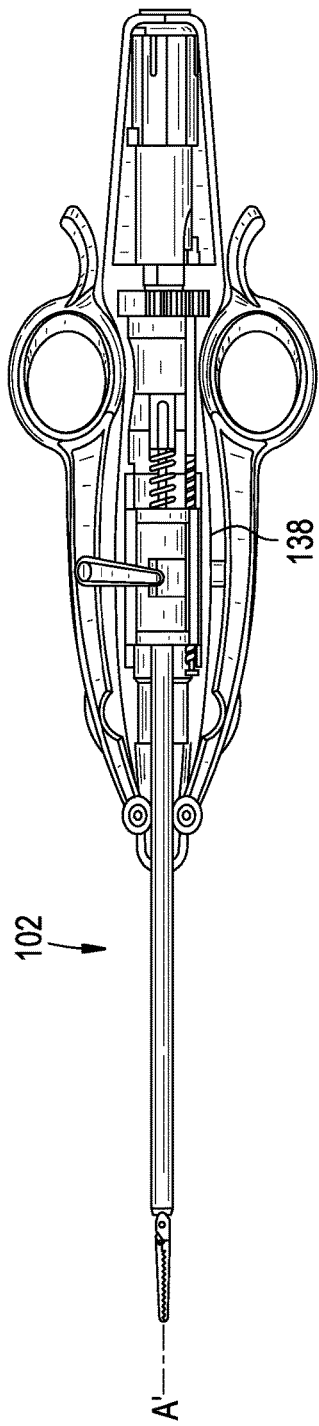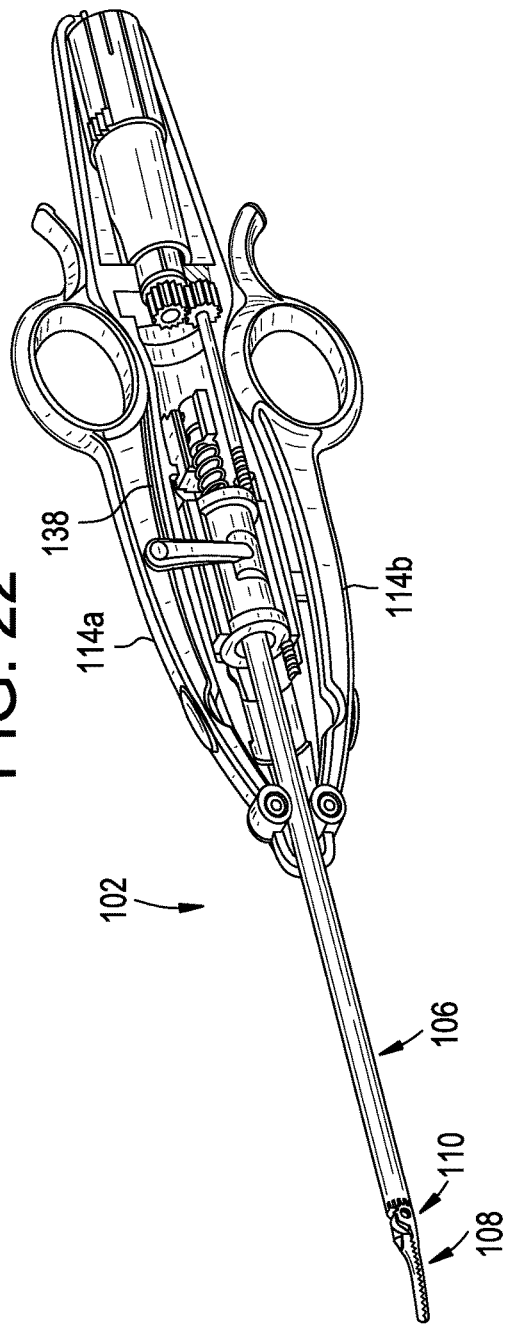

SURGICAL DEVICES WITH ARTICULATING END EFFECTORS AND METHODS OF USING SURGICAL DEVICES WITH ARTICULATING END EFFECTORS

CROSS-REFERENCE TO RELATED APPLICATIONS

This application is a continuation of U.S. patent application Ser. No. 14/230,027 filed on Mar. 31, 2014, entitled "Surgical Devices with Articulating End Effectors and Methods of Using Surgical Devices with Articulating End Effectors, which is hereby incorporated by reference in its entirety.

FIELD

The present invention relates to surgical devices with articulating end effectors and methods of using surgical devices with articulating end effectors.

BACKGROUND

Minimally invasive surgical techniques such as endoscopies and laparoscopies are often preferred over traditional surgeries because the recovery time, pain, and surgery-related complications are typically less with minimally invasive surgical techniques. Rather than cut open large portions of the body in order to access inner cavities, surgeons either rely on natural orifices of the body or create one or more small orifices in which surgical instruments can be inserted to allow surgeons to visualize and operate at the surgical site.

Some minimally invasive procedures can require that a working end of a device, which is inserted into the body, be articulated to angularly reorient the working end relative to the tissue. During such a procedure, for example, it is often necessary to reorient the working end such that jaws at the working end are at an angle relative to a shaft of the device, while still allowing the jaws to open and close to grasp tissue. Such angulation is often achieved via one or more cables attached to the jaws. However, with current cable driven jaw reorienting actuation systems, after articulation of the device, the cables are subject to high tensions which makes opening and closing of the jaws with precision difficult.

Accordingly, there remains a need for improved surgical devices with articulating end effectors and methods of using surgical devices with articulating end effectors.

SUMMARY

A surgical device is provided that in one embodiment includes a proximal handle portion, a first elongate shaft extending distally from the proximal handle portion, a second elongate shaft extending distally from the proximal handle portion and being disposed within a first passageway of the first elongate shaft, a third elongate shaft extending distally from the proximal handle portion and being disposed within a second passageway of the second elongate shaft, a first jaw having a proximal end operatively connected to a distal end of the first elongate shaft, and a second jaw having a proximal end operatively connected to a distal end of the second elongate shaft. The first and second elongate shafts can be configured to simultaneously rotate about a longitudinal axis of the third elongate shaft with the third elongate shaft being stationary relative thereto. The rotation of the first and second elongate shafts can angularly orient the first and second jaws relative to the longitudinal axis of the third elongate shaft.

The device can have any number of additional features and/or variations. For example, the first and second jaws can be configured to angularly orient in a same direction relative to the longitudinal axis of the third elongate shaft in response to the first elongate shaft rotating in a first direction simultaneously with the second elongate shaft rotating in a second direction that is opposite to the first direction. For another example, the first and second jaws can be configured to move away from one another in response to the first and second elongate shafts simultaneously rotating in a same direction. For yet another example, the proximal end of the first jaw can be attached to the third elongate shaft at a pivot point, the proximal end of the second jaw can be attached to the third elongate shaft at the pivot point, and angularly orienting the first and second jaws relative to the longitudinal axis of the third elongate shaft can include pivoting the first and second jaws at the pivot point.

In another embodiment, a surgical device is provided that includes a proximal handle portion, an outer tube extending distally from the handle portion, an inner tube extending distally from the proximal handle portion and being disposed within a passageway of the outer tube, a first jaw having a proximal end operatively connected to a distal end of the outer tube, a second jaw having a proximal end operatively connected to a distal end of the inner tube, and an actuator coupled to the handle portion and configured to be actuated so as to simultaneously rotate the inner and outer tubes, thereby articulating the first and second jaws relative to a common longitudinal axis of the inner and outer tubes.

The device can have any number of additional features and/or variations. For example, the actuation of the actuator can cause the inner tube to rotate in a first direction and the outer tube to rotate in a second direction that is opposite to the first direction. For another example, the actuator can include a knob configured to be actuated by being rotated in a first direction, thereby causing the outer tube to rotate in the first direction and causing the inner tube to rotate in a second, opposite direction, and configured to be actuated by being rotated in the second direction, thereby causing the outer tube to rotate in the second direction and causing the inner tube to rotate in the first direction. For another example, the device can include a first helical gear operatively connected to the outer tube, and a second helical gear operatively connected to the inner tube. The actuation of the actuator can cause the first helical gear to rotate in a first direction so as to cause the outer tube to rotate in the first direction and can cause the second helical gear to rotate in a second direction that is opposite to the first direction so as to cause the inner tube to rotate in the second direction. For another example, the device can include a movement assembly including a sleeve, a bushing disposed within the sleeve, a first helical gear operatively connected to the outer tube and threadably engaged with the bushing, and a second helical gear operatively connected to the inner tube and threadably engaged with the bushing. The actuator can be operatively connected to the movement assembly such that the actuation of the actuator can cause the sleeve and the bushing to translate along the common longitudinal axis and can cause the first and second helical gears to rotate about the common longitudinal axis. For another example, the device can include a rod extending distally from the proximal handle portion and being disposed within a passageway of the inner tube. The inner and outer tubes can simultaneously rotate relative to the rod in response to the actuation of the actuator. The first and second jaws can articulate relative to the rod in response to the actuation of the actuator. For another example, the device can include a motor, and the actuation of the actuator causing the motor to drive the rotation of the inner and outer tube. The actuator can include a switch configured to electrically communicate with the motor.

For another example, the device can include a second actuator coupled to the proximal handle portion and configured to be actuated so as to simultaneously rotate the inner and outer tubes, thereby causing the first and second jaws to selectively open and close. The second actuator can include first and second handles configured to move toward and away from one another, thereby causing the outer tube and the inner tube to both rotate in a same direction. The device can include a first helical gear operatively connected to the outer tube, and a second helical gear operatively connected to the inner tube. The actuation of the second actuator can cause the first and second helical gears to each rotate in one of a clockwise direction and a counterclockwise direction so as to cause the inner and outer tubes to each rotate in the one of the clockwise direction and the counterclockwise direction. The device can include a movement assembly including a sleeve, a bushing disposed within the sleeve, a first helical gear operatively connected to the outer tube and threadably engaged with the bushing, and a second helical gear operatively connected to the inner tube and threadably engaged with the bushing. The actuator can be operatively connected to the movement assembly such that the actuation of the actuator can cause the sleeve and the bushing to translate along the common longitudinal axis and causes the first and second helical gears to rotate about the common longitudinal axis. The second actuator can be operatively connected to the movement assembly such that the actuation of the second actuator can cause the bushing to rotate relative to the sleeve and causes the first and second helical gears to rotate about the common longitudinal axis.

In another embodiment, a surgical device is provided that includes a first jaw coupled to a first drive mechanism configured to rotate about a first longitudinal axis of the first drive mechanism, and a second jaw coupled to a second drive mechanism configured to rotate about a second longitudinal axis of the second drive mechanism. The second drive mechanism can be independent of the first drive mechanism. The surgical device can also include a motor operatively connected to the first and second drive mechanisms and configured to cause synchronous rotation of the first and second drive mechanisms so as to either drive the first and second jaws to selectively open and close, or drive the first and second jaws to articulate in a same direction as one another.

The device can have any number of additional features and/or variations. For example, the first and second drive mechanisms can each include a rigid tubular shaft. For another example, the surgical device can include a proximal handle portion. The first and second drive mechanisms can each extend distally from the proximal handle portion, and the first and second jaws can be coupled to respective distal ends of the first and second drive mechanisms. For yet another example, the first and second longitudinal axes can be coaxial. For another example, the first and second longitudinal axes can be parallel to one another.

In another aspect, a surgical method is provided that in one embodiment includes advancing jaws located at a distal end of a surgical instrument into a body. The surgical instrument can include a handle, an outer tube extending distally from the handle, and an inner tube disposed within the outer tube and extending distally from the handle. The surgical method can also include actuating a first actuator coupled to the handle so as to cause the inner and outer tubes to rotate in opposite directions, thereby causing the jaws to articulate in a same direction as one another. The surgical method can also include actuating a second actuator coupled to the handle so as to cause the inner and outer tubes to rotate in a same direction, thereby causing the jaws to selectively open and close.

The method can have any number of additional features and/or variations. For example, actuating the first actuator can include rotating the first actuator in a first direction or in a second direction that is opposite to the first direction, the rotation of the first actuator in the first direction causing the outer tube to rotate in the first direction and causing the inner tube to rotate in the second direction, and the rotation of the first actuator in the second direction causing the outer tube to rotate in the second direction and causing the inner tube to rotate in the first direction. For another example, actuating the first actuator can cause a motor to drive the rotation of the inner and outer tube in the opposite directions. For a further example, the second actuator can include first and second handles, and actuating the second actuator can include moving the first and second handles toward and away from one another.

BRIEF DESCRIPTION OF DRAWINGS

This invention will be more fully understood from the following detailed description taken in conjunction with the accompanying drawings, in which:

FIG. 20 is a perspective view of another embodiment of a surgical device;

FIG. 21 is a side partial cross-sectional view of the surgical device of FIG. 20;

FIG. 22 is a perspective cross-sectional view of the surgical device of FIG. 20.

DETAILED DESCRIPTION

Figure 1:
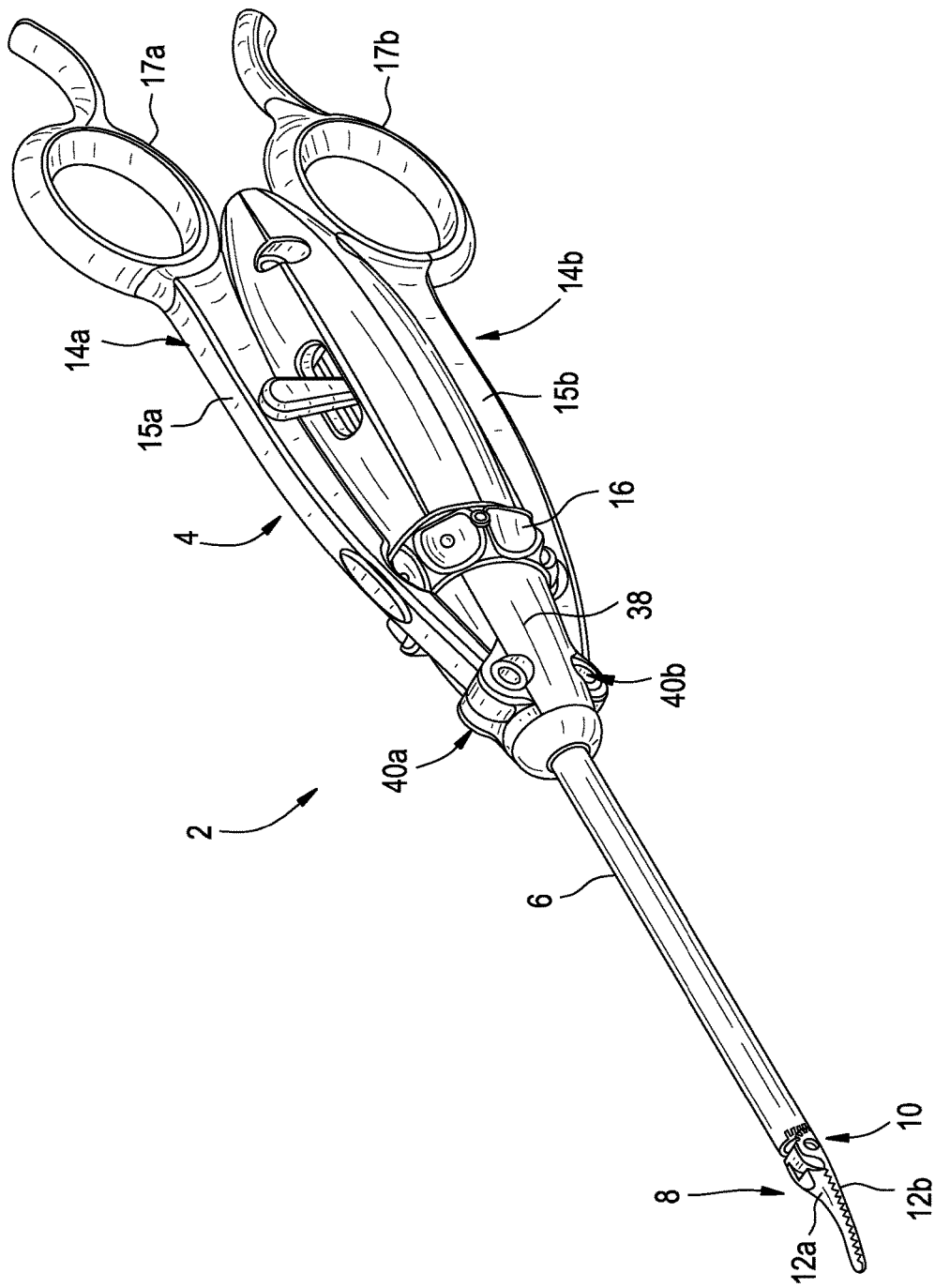
FIG. 1 is a perspective view of one embodiment of a surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary surgical devices with articulating end effectors and methods of using surgical devices with articulating end effectors are provided. In general, the surgical devices with articulating end effectors and methods of using surgical devices with articulating end effectors can provide rotary driven pivoting of the end effector. In some embodiments, the device can include a handle, a first tube extending distally from the handle, a second tube extending distally from the handle and being disposed within the first tube, and an end effector that includes a pair of distal jaws configured to move in response to rotation of the first tube about a longitudinal axis thereof and rotation of the second tube about a longitudinal axis thereof. The handle can include at least one actuator configured to be actuated by a user so as to cause the rotation of the first and second tubes. The jaws can be configured to move in two different ways depending on whether the first and second tubes are rotating in a same direction as one another or in different ways than each other. In response to the first and second tubes rotating in a same direction as one another, e.g., both clockwise or both counterclockwise, the jaws can be configured to move by opening and closing, e.g., by moving toward and away from one another, which can facilitate clamping of tissue and/or other material between the jaws. In response to the first and second tubes rotating in different directions from one another, e.g., one clockwise and the other counterclockwise, the jaws can be configured to articulate together relative to the longitudinal axes of the first and second tubes, which can facilitate angular positioning of the jaws relative to a tissue and/or other target to be clamped by the jaws. The jaws can thus be configured to be opened/closed and articulated using the same mechanical mechanism, e.g., the first and second tubes, which can simplify manufacturing and/or reduce monetary cost of the device by allowing for a fewer number of parts and less complex mechanical connections than if separate mechanisms were provided for articulating the jaws and for opening/closing the jaws. A proximal end of one of the jaws can be attached to a distal end of the outer tube, and a proximal end of the other of the jaws can be attached to a distal end of the inner tube, which can facilitate the movement of the jaws in response to the rotation of the inner and outer tubes. The attachment of the proximal ends of the jaws to respective ones of the inner and outer tubes can help provide high torque, speed, and strength for the movement of the jaws, e.g., because the inner and outer tubes are located proximal to the jaws throughout movement of the jaws and do not extend across or bend at a pivot point about which the jaws rotate to open/close and to articulate. The device can be powered, e.g., tube rotation driven using a motor, or the device can be non-powered, e.g., mechanically driven tube rotation.

Figure 2:
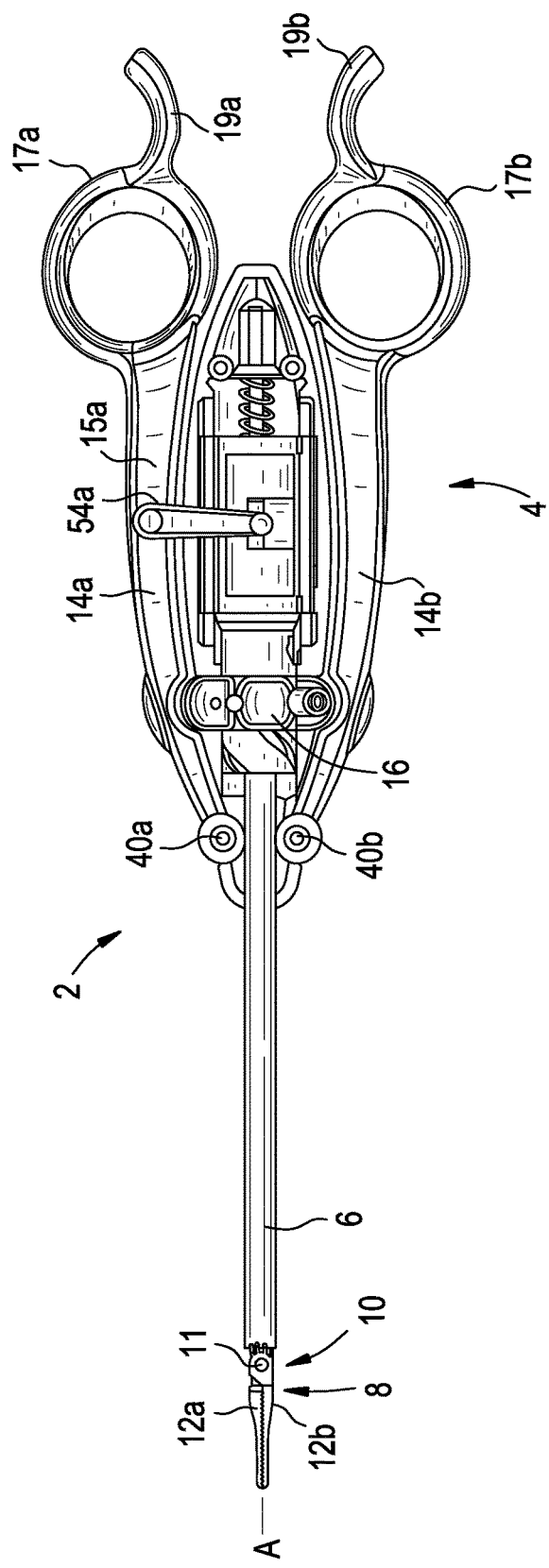
FIG. 2 is a side, partial cross-sectional view of the surgical device of FIG. 1.

In an exemplary embodiment, shown in FIGS. 1 and 2, a surgical device 2 can include a proximal handle portion 4 having an elongate shaft 6 extending distally therefrom. The shaft 6 can have a working element 8, also referred to herein as an "end effector," at a distal end thereof. The end effector 8 can be coupled to the shaft 6 at a pivot joint 10. A proximal end of the end effector 8 can be pivotally coupled to the joint 10 at a distal end of the shaft 6. The end effector 8 in this illustrated embodiment includes a tissue grasper having a pair of opposed jaws 12a, 12b configured to move between open and closed positions. The end effector 8 can have other configurations, e.g., scissors, a babcock, etc. The jaws 12a, 12b can also be configured to move between articulated positions where the jaws 12a, 12b are angled relative to a longitudinal axis A of the shaft 6 so as to reorient the jaws 12a, 12b relative thereto. As discussed further below, the handle portion 4 can include a first actuator configured to effect the opening and closing of the opposed jaws 12a, 12b, e.g., movement of the jaws 12a, 12b toward and away from one another. The handle portion 4 can also include a second actuator 16 configured to effect the articulation of the opposed jaws 12a, 12b, e.g., movement of both jaws 12a, 12b in a same direction relative to the shaft's longitudinal axis A. The articulation can be independent of the opening and closing of the jaws 12a, 12b.

Figure 3:
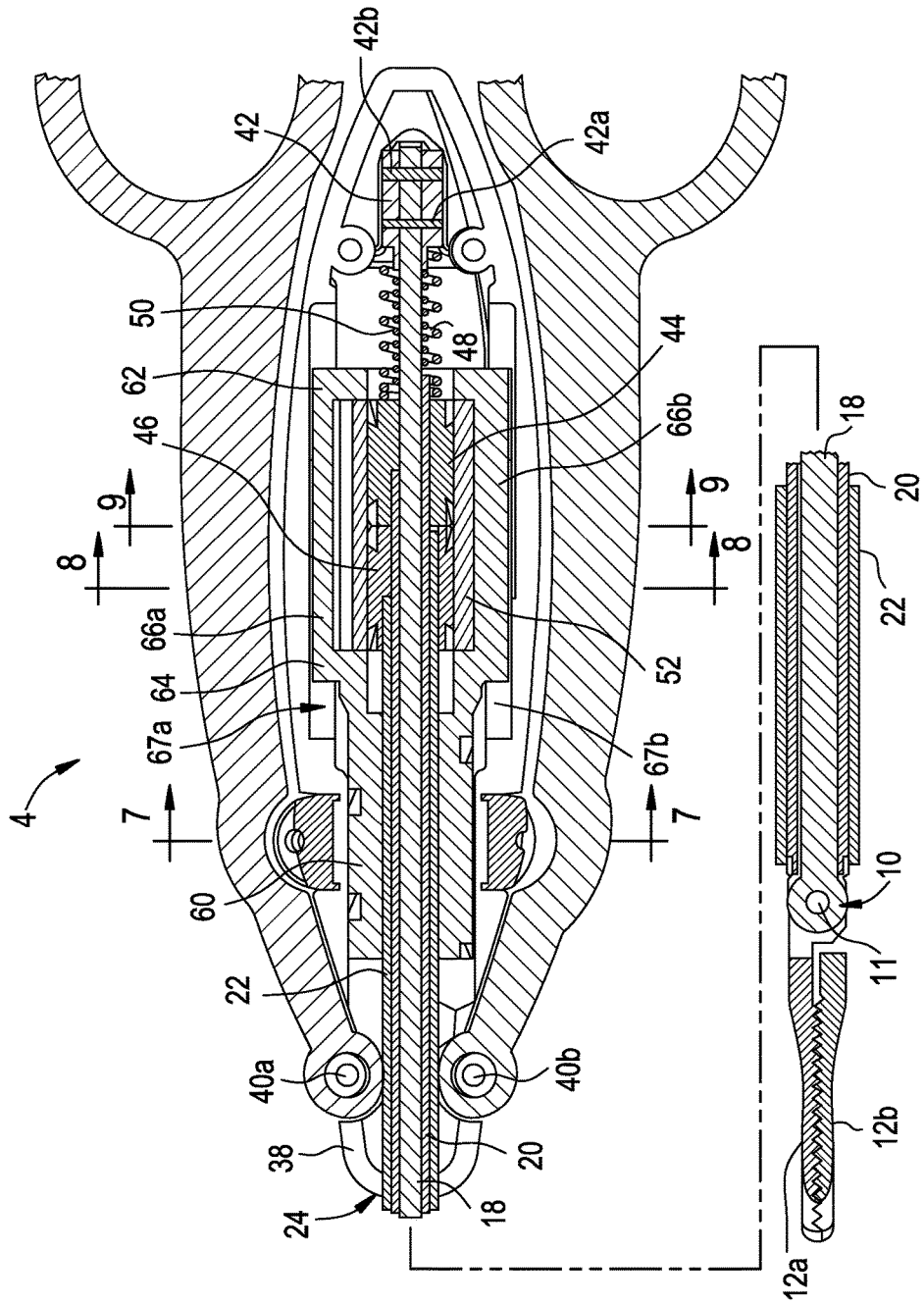
FIG. 3 is a partial side, cross-sectional view of the surgical device of FIG. 1.
Figure 4:
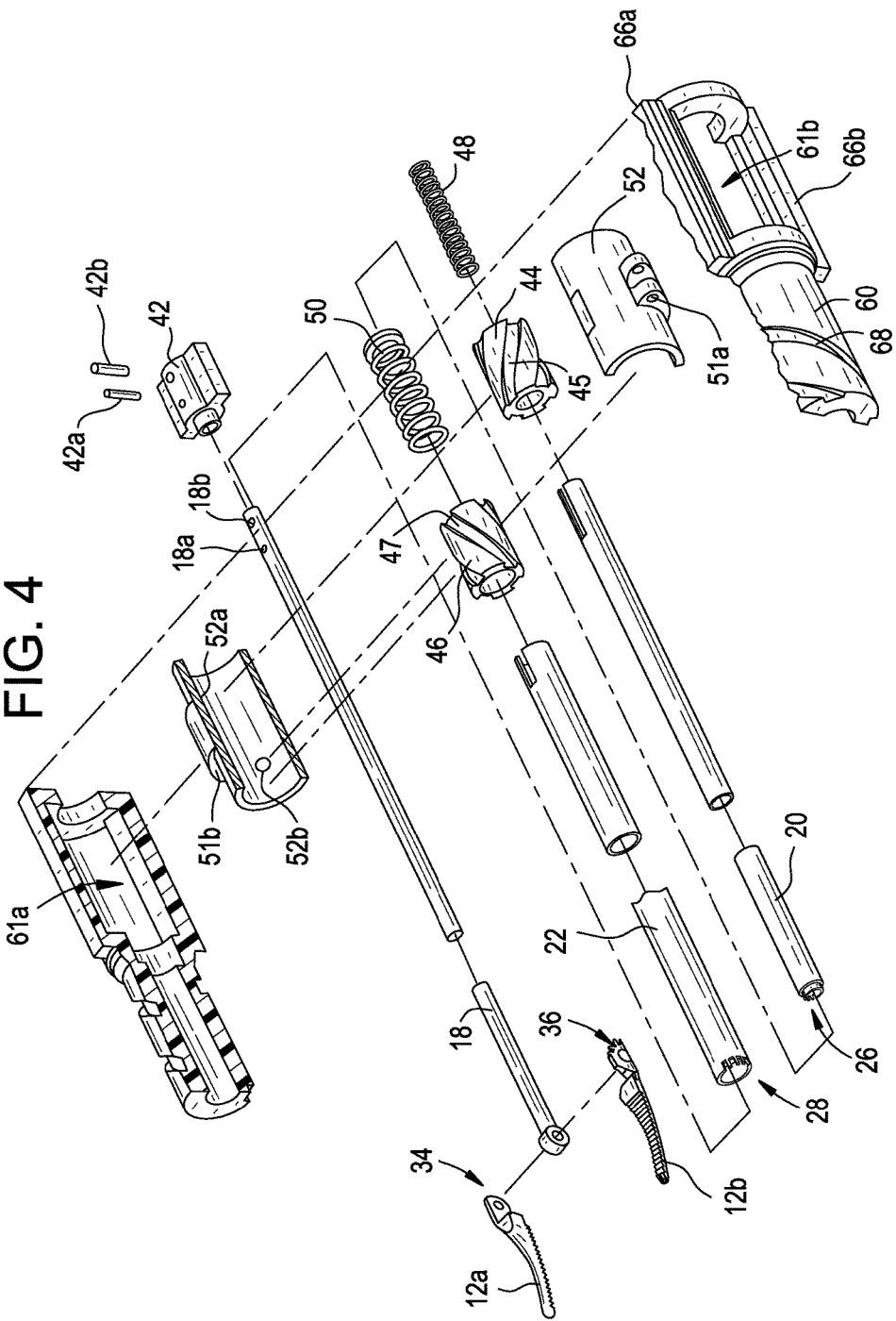
FIG. 4 is an exploded view of components at least partially disposed within a housing of the surgical device of FIG. 1, and an end effector of the surgical device of FIG. 1.
Figure 7:
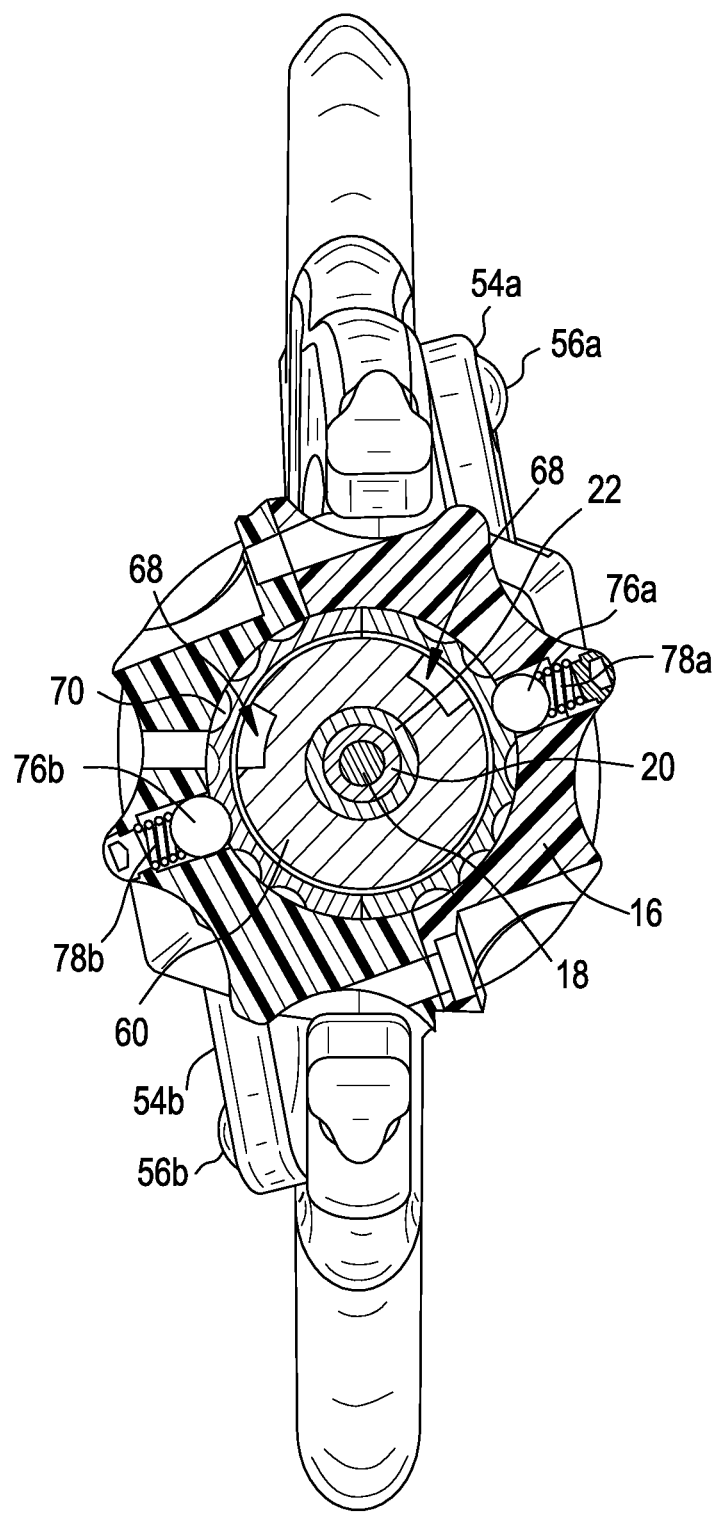
FIG. 7 is a cross-sectional view of the surgical device of FIG. 3.
Figure 8:
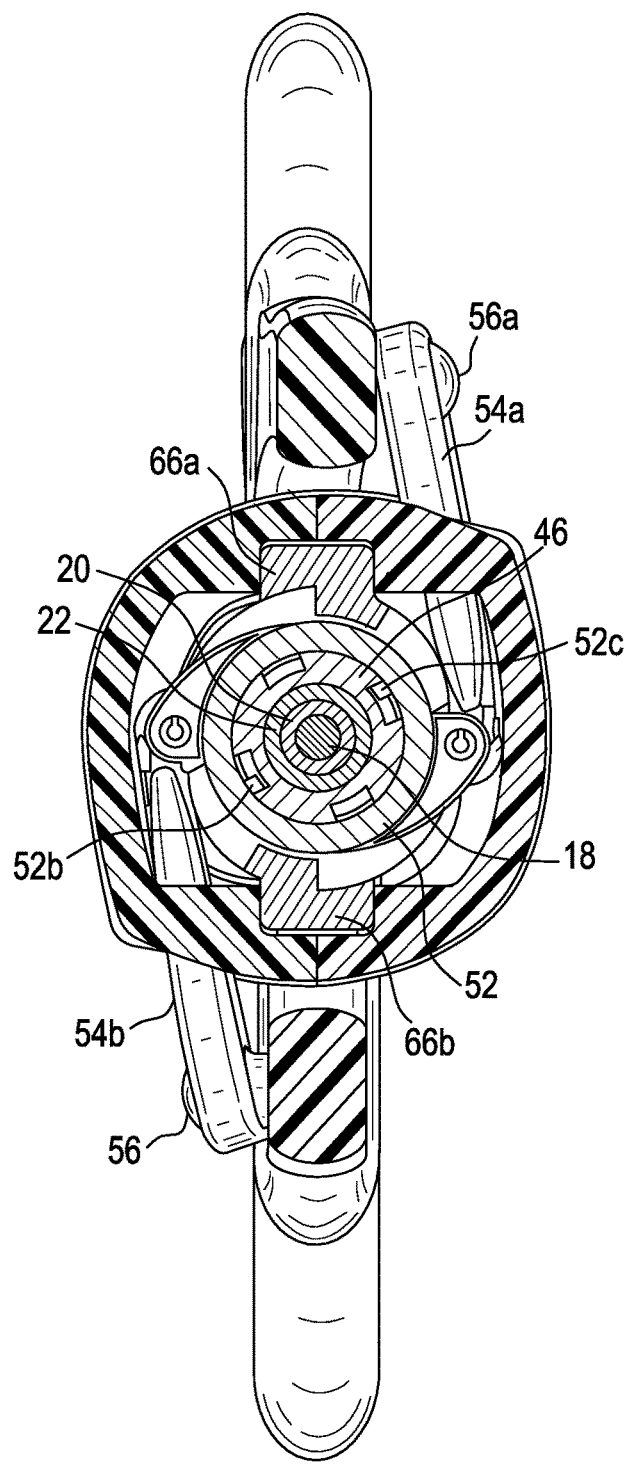
FIG. 8 is another cross-sectional view of the surgical device of FIG. 3.

The shaft 6 can have a variety of sizes, shapes, and configurations. In an exemplary embodiment, the shaft 6 can be rigid, e.g., made from a generally non-bendable material such as a metal (e.g., stainless steel, titanium, etc.) or a hard polymer. As shown in FIGS. 3 and 4, the shaft 6 can include a central shaft 18, an inner tubular shaft 20, and an outer tubular shaft 22. The central shaft 18, the inner tubular shaft 20, and the outer tubular shaft 22 can be coaxial with one another such that they all share the same longitudinal axis A, as in this illustrated embodiment, as shown in FIGS. 3, 7, and 8. Generally, the central shaft 18 can be configured to remain stationary relative to the handle portion 4, to the inner tubular shaft 20, and to the outer tubular shaft 22. The inner tubular shaft 20 and the outer tubular shaft 22 can be configured to move relative to the handle portion 4, to the central shaft 18, and to each other, as discussed further below.

The shaft 6 can have any longitudinal length, although in an exemplary embodiment it can be long enough to allow the handle portion 4 to be manipulated outside a patient's body while the shaft 6 extends through an opening in the body with the end effector 8 disposed within a body cavity, e.g., have a longitudinal length of about 33 cm. In this way, the end effector 8 can be easily manipulated when the device 2 is in use during a surgical procedure. The shaft 6 can have any diameter. For example, the shaft's diameter can be less than or equal to about 10 mm, e.g., less than or equal to about 7 mm, less than or equal to about 5 mm, etc., which can allow for insertion of the shaft 6 through an minimally invasive access device, such as during a laparoscopic surgical procedure. The end effector 8 mated to the shaft's distal end can have a diameter equal to or less than the shaft's diameter, at least when the jaws 12a, 12b are in the closed position, which can facilitate insertion of the device's distal portion into a patient's body.

Figure 5:
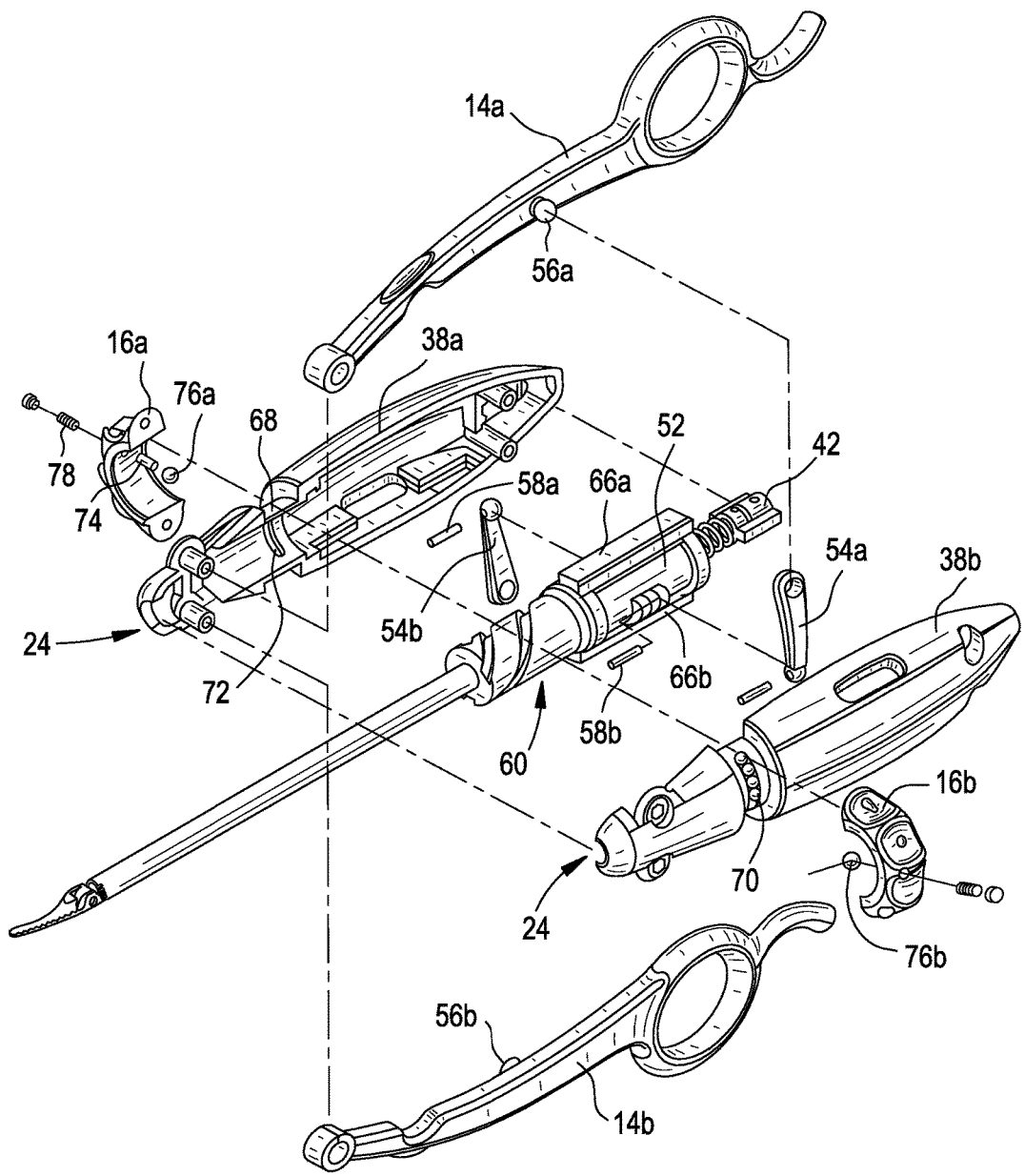
FIG. 5 is an exploded view of the surgical device of FIG. 1.

The central shaft 18 can have a variety of sizes, shapes, and configurations. In an exemplary embodiment, the central shaft 18 can be rigid. The central shaft 18 can be fixedly attached to the handle portion 4, e.g., at a proximal end of the central shaft 18, so as to be in a fixed position relative to the handle portion 4. The central shaft 18 can extend from the handle portion 4 through a distal opening 24 defined by a main housing 38 of the handle portion 4, as shown in FIGS. 2, 3, and 5. A distal end of the central shaft 18 can define the pivot joint 10 at which the jaws 12a, 12b can be pivotally attached to the shaft 6. The jaws 12a, 12b can be attached to the central shaft 18 via a pin 11 (the pin 11 is not shown in FIG. 4). The end effector 8 can be mechanically attached to the inner and outer tubular shafts 20, 22 at locations proximal to the joint 10, as discussed further below.

Figure 6:
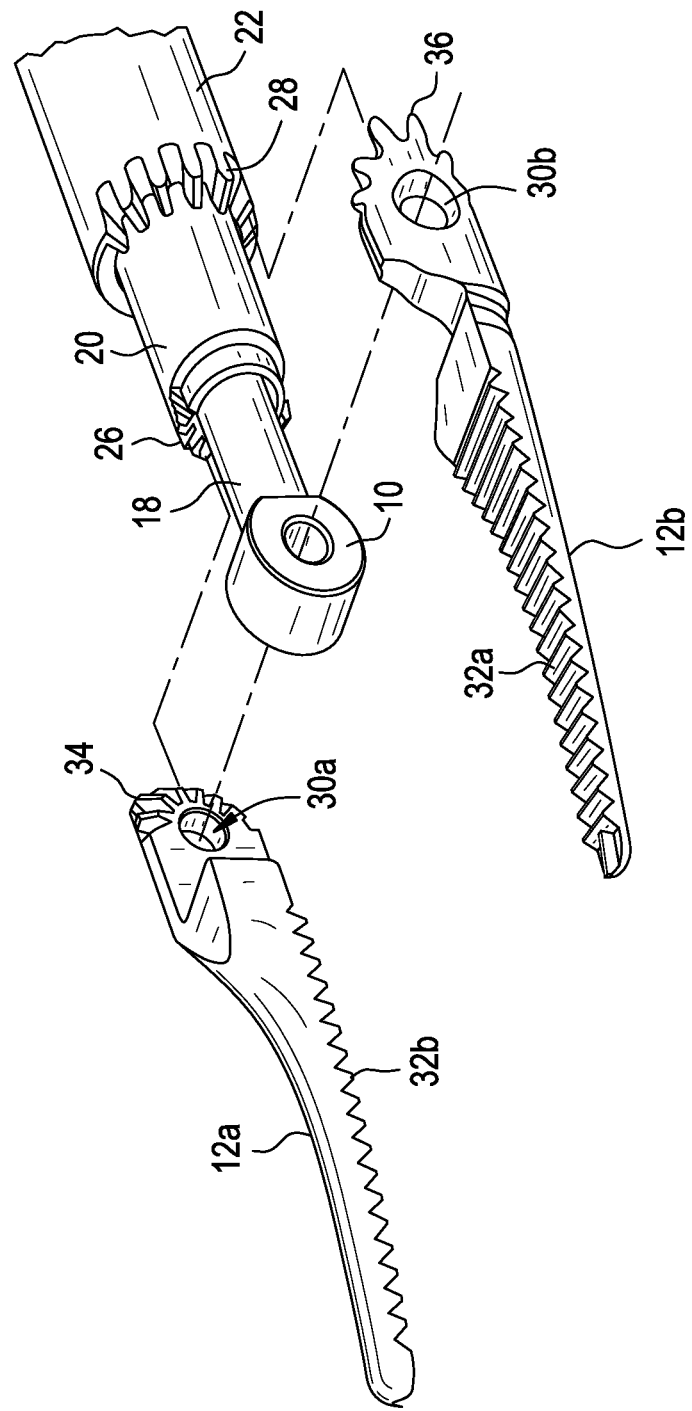
FIG. 6 is an exploded view of an end effector of the surgical device of FIG. 1 and of a distal portion of an elongate shaft of the surgical device of FIG. 1.

The inner tubular shaft 20, also referred to herein as an "inner tube," can have a variety of sizes, shapes, and configurations. In an exemplary embodiment, the inner tube 20 can be rigid. The inner tube 20 can have its distal end located proximal to the joint 10, e.g., proximal to the distal end of the central shaft 18, as shown in FIGS. 3 and 6, which can facilitate pivoting of a first, top one of the jaws 12a about the joint 10. The inner tube 20 can be freely rotatable relative to the outer tubular shaft 22 and the central shaft 18 about the longitudinal axis A. A proximal portion of the inner tube 20 can extend into the handle portion 4 with a proximal end thereof position within the handle portion 4, as shown in FIG. 3. The inner tube 20 can extend distally from the housing 38 through the distal opening 24 of the handle portion 4. As shown in FIGS. 4 and 6, the inner tube 20 can have teeth 26 extending partially around a circumference of the distal end thereof. The teeth 26 can be operatively engaged with the first jaw 12a, as discussed further below. A number of the teeth 26 can vary based on factor(s) such as a size of the teeth, a size of the inner tube 20, a shape of the teeth 26, etc.

The outer tubular shaft 22, also referred to herein as an "outer tube," can have a variety of sizes, shapes, and configurations. In an exemplary embodiment, the outer tube 22 can be rigid. The outer tube 22 can be freely rotatable relative to the inner tube 20 and the central shaft 18 about the longitudinal axis A. A proximal portion of the outer tube 22 can extend into the handle portion 4 with a proximal end thereof positioned within the handle portion 4, as shown in FIG. 3. The outer tube 22 can extend distally from the housing 38 through the distal opening 24 of the handle portion 4. As shown in FIGS. 4 and 6, the outer tube 22 can have teeth 28 extending partially around a circumference of a distal end thereof. A number of the teeth 28 can vary based on factor(s) such as a size of the teeth, a size of the outer tube 22, a shape of the teeth 28, etc. The outer tube's teeth 28 can be operatively engaged with a second, bottom one of the jaws 12b. The teeth 28 formed on the outer tube 22 can be on an opposite side of the shaft 6 than the teeth 26 formed on the inner tube 20. For example, as shown in FIG. 6, the outer tube's teeth 28 can be formed on a left side of the shaft 6, and the inner tube's teeth 26 can be formed on a right side of the shaft 6. In another embodiment, the outer tube's teeth 28 can be formed on a right side of the shaft 6, and the inner tube's 26 teeth can be formed on a left side of the shaft 6.

In some embodiments, only one of the inner and outer tubes can have teeth formed thereon, and only one of the jaws can have corresponding teeth operatively engaged therewith. In this way, instead of both the first and second jaws 12a, 12b being moveable in response to movement of the inner and outer tubes 20, 22 as in the illustrated embodiment of FIG. 1, only one of the jaws can be moveable (the jaw with teeth) relative to the central shaft 18 while the other jaw is configured to remain stationary relative to the central shaft 18.

The end effector 8 can have a variety of sizes, shapes, and configurations. In an exemplary embodiment, the end effector 8 can be rigid. As shown in FIG. 1, the end effector 8, including the first and second jaws 12a, 12b, can be disposed at a distal end of the surgical device 2. The end effector 8 can include the first jaw 12a and the second jaw 12b pivotally connected to the central shaft 18 at the joint 10. As shown in FIG. 6, each of the first jaw 12a and the second jaw 12b can include a gripping feature 32a, 32b, respectively, on tissue engaging surfaces of the jaws 12a, 12b. The gripping features 32a, 32b can contact one another when the end effector 8 is in a closed position and the end effector 8 is not holding tissue and/or other matter therebetween, as shown in FIGS. 1, 3, and 5. In other embodiments, the gripping features 32a, 32b may not contact one another when the end effector 8 is closed, e.g., the tissue engaging surfaces of the jaws 12a, 12b have a space therebetween when the jaws 12a, 12b are fully closed. The gripping feature 32a, 32b can be configured to provide the end effector 8 with a greater ability to grip tissue and/or other matter between the jaws 12a, 12b. This enhanced gripping ability can be accomplished via an increased coefficient of friction of the gripping features 32a, 32b. The gripping features 32a, 32b can include a plurality of ridges, as in this illustrated embodiment. The gripping features 32a, 32b can have other configurations, such as a plurality of bumps, a textured surface, a roughened surface, and/or other enhanced coefficient of friction enhancing surfaces. The first jaw 12a and the second jaw 12b can each have a pivot hole 30a, 30b, respectively, at proximal ends thereof that facilitate securing of the jaws 12a, 12b to the pivot joint 10 via the pin 11 that can be positioned within the pivot holes 30a, 30b (the pin 11 is not shown in FIG. 6).

The first jaw 12a at the proximal end thereof can have a rounded profile about the pivot hole 30a. The first jaw 12a can have teeth 34 which are defined in the rounded profile.

The first jaw's teeth 34 can be configured to operatively mate with the teeth 26 of the inner tube 20. Upon rotation of the inner tube 20, the teeth 26 of the inner tube 20 can moveably engage the teeth 34 of the first jaw 12a so as to rotate the first jaw 12a about the joint 10 so as to angularly adjust the first jaw 12a relative to the shaft's longitudinal axis A. The rotation of the first jaw 12a can be independent of the rotation of the second jaw 12b, as discussed further below.

The second jaw 12b can generally be configured similar to the first jaw 12a, except the second jaw 12b can be operatively mated to the outer tube 22 instead of the inner tube 20. The second jaw 12b at the proximal end thereof can have a rounded profile about the pivot hole 30b. The second jaw 12b can have teeth 36 which are defined in the rounded profile. The second jaw's teeth 36 can be configured to operatively mate with the teeth 28 of the outer tube 22. Upon rotation of the outer tube 22, the teeth 28 of the outer tube 22 can moveably engage the teeth 36 of the second jaw 12b so as to rotate the second jaw 12b about the joint 10 so as to angularly adjust the second jaw 12b relative to the shaft's longitudinal axis A. The rotation of the second jaw 12b can be independent of the rotation of first jaw 12a since the second jaw's movement can be controlled by movement of the outer tube 22 while movement of the first jaw 12a can be controlled by movement of inner tube 20. In this way, the first jaw 12a can be configured to move in response to movement of the inner tube 20, and the second jaw 12b can be configured to move in response to movement of the outer tube 22.

The handle portion 4 can have a variety of sizes, shapes, and configurations. The handle portion 4 can include the main housing 38, which can house a variety of elements therein and can have some elements accessible outside thereof, such as the first actuator and the second actuator. The main housing 38 can include first and second halves 38a, 38b, as shown in FIG. 5. The halves 38a, 38b can be fixedly attached together, e.g., fixed together during manufacturing of the device 2, which can help protect the elements disposed therein.

In an exemplary embodiment, the first actuator can include first and second gripper arms 14a, 14b, also referred to herein as "handles." As shown in FIGS. 1-3, each of the gripper arms 14a, 14b can be pivotally attached to the main housing 38 at a handle pivot point 40a, 40b, respectively. Each of the arms 14a, 14b can include an elongate member 15a, 15b, respectively, each having a finger loop 17a, 17b and a thumb rest 19a, 19b, similar to scissors. The arms 14a, 14b can, in other embodiments, have different sizes, shapes, and configurations, e.g., no thumb rests, multiple finger loops, different arcuate shape, etc. The arms 14a, 14b can be configured to move toward and away from the main housing 38, thereby actuating the inner and outer tubes 20, 22 and hence the end effector 8. The arms 14a, 14b can be operatively connected to the inner and outer tubes 20, 22 such that actuation of the arms 14a, 14b, e.g., manual movement thereof by a user, can cause movement of the inner and outer tubes 20, 22. As discussed further below, actuation of the first actuator 14a, 14b can cause the inner and outer tubes 20, 22 to each rotate in a same direction about the shaft's longitudinal axis A.

In an exemplary embodiment, the second actuator can include an articulation knob 16. The articulation knob 16 can have a variety of sizes, shapes, and configurations. The articulation knob 16 can be rigid. The articulation knob 16 can include a moveable ring. The articulation knob 16 can be proximal to the pivot points 40a, 40b of the handles 14a, 14b, as in this illustrated embodiment. The articulation knob 16 can be two separate semi-circular parts 16a, 16b that can be fixedly assembled together, e.g., during manufacturing, or the knob 16 can be a singular piece as in this illustrated embodiment. The articulation knob 16 can be rotatably coupled to the main housing 38. The articulation knob 16 can sit in a recess 68 formed in the housing 38, as shown in FIG. 5. The articulation knob 16 can include at least one pin 74 extending radially inward therefrom, e.g., extending radially inward from an interior surface thereof. The articulation knob 16 includes a single pin 74 in this illustrated embodiment, as shown in FIG. 5, but the knob 16 can include multiple pins. The housing 38 can have at least one slot 72 formed therein, e.g., in the recess 68, that can be configured to have the at least one pin 74 extending therethrough. The at least one pin 74 can be configured to slide within the at least one slot 72 when the knob 16 is actuated, e.g., rotated.

The articulation knob 16 can include one or more finger depressions on an exterior surface thereof, as in this illustrated embodiment. The finger depressions can facilitate manual movement of the knob 16 using one or more fingers seated in the finger depressions. The finger depressions in this illustrated embodiment extend around an entire circumference of the knob's exterior surface.

The articulation knob 16 can include at least one detent ball 76a, 76b. The knob 16 includes two detent balls 76a, 76b in this illustrated embodiment, as shown in FIGS. 5 and 7. Each of the detent balls 76a, 76b can each be sized to fit within a bore formed within the articulation knob 16. The at least one detent ball 76a, 76b can be biased radially inward by at least one spring 78a, 78b. The articulation knob 16 includes two springs 78a, 78b in this illustrated embodiment, one for each of the detent balls 76a, 76b. Each of the detent balls 76a, 76b can be configured to be seated in one of a plurality of corresponding detent depressions 70 formed in the housing 38 in the recess 68 in which the knob 16 can be seated. The detent depressions 70 can extend around at least a partial circumference of the recess 68, as shown in FIGS. 5 and 7. The detent balls 76a, 76b and the detent depressions 70 can cooperate to help hold the articulation knob 16 in a selected rotational position relative to the housing 38, and hence help hold the jaws 12a, 12b in a selected articulated position relative to the shaft 6. As the knob 16 is rotated about the longitudinal axis A, the detent ball 76a, 76b can move between being seated in adjacent ones of the detent depressions 70, which can hold the detent balls 76a, 76b therein so as to restrain the knob 16 from freely rotating, without actuation thereof by a user. The movement of the detent balls 76a, 76b between adjacent depressions 70 can be palpably felt by a user manually moving the knob 16, which can help the user controllably and predictably move the knob 16 and hence controllably and predictably articulate the end effector 8. Each of the depressions 70 can correspond to one articulated position of the end effector 8.

The articulation knob 16 can be operatively connected to the inner and outer tubes 20, 22 such that actuation of the articulation knob 16, e.g., manual movement thereof by a user, can cause movement of the inner and outer tubes 20, 22. The movement of the inner and outer tubes 20, 22 in response to the knob's 16 movement can be in a different manner than the movement of the inner and outer tubes 20, 22 caused by the first actuator 14a, 14b. As discussed further below, activation of the second actuator 16 can cause the inner and outer tubes 20, 22 to rotate in an opposite directions from one another, e.g., one clockwise and the other counterclockwise, about the shaft's longitudinal axis A.

In an exemplary embodiment, the articulation knob 16 can be configured to be actuated so as to cause the jaws 12a, 12b to articulate about ±60°. In other words, the articulation knob 16 can be configured to articulate the end effector 8 upward 60° relative to the longitudinal axis A and downward 60° relative to the longitudinal axis A.

As mentioned above, a proximal portion of the central shaft 18 can be disposed within the housing 38. As shown in FIGS. 3 and 4, the central shaft 18 can be attached to an anchor member 42 disposed within the housing 38. The anchor member 42 can be configured to prevent the central shaft 18 from rotating or otherwise moving relative to the housing 38. The anchor member 42 can be attached to interior surfaces of the housing halves 38a, 38b, as shown in FIG. 5, so as to secure the central shaft 18 in a fixed position relative to the housing 38. The anchor member 42 can be attached to the central shaft 18 via one or more anchor pins 42a, 42b. The central shaft 18 can, at the proximal end thereof, have one or more through holes 18a, 18b formed therein into which the one or more anchor pins 42a, 42b can be disposed to secure the central shaft 18 to the anchor member 42. The central shaft 18 can additionally or alternatively be attached to the housing 38 in other ways, such as by being welded thereto, adhered thereto using adhesive, molded therewith, etc.

The central shaft 18 can have an inner tube bias member 48 and an outer tube bias member 50 disposed therearound. The bias members 48, 50 can be located distal to the anchor member 42, as in this illustrated embodiment. The bias members 48, 50 can be coaxial, and the inner tube bias member 48 can be disposed within the outer tube bias member 50, as shown in FIG. 3. The bias members 48, 50 are each coil springs in the illustrated embodiment, but the bias members 48, 50 can have other configurations, e.g., a volute spring, a flat spring, a rubber band, etc. A proximal end of the inner tube bias member 48 can abut the anchor member 42, and a distal end of the inner tube bias member 48 can abut the proximal end of the inner tube 20. The inner tube bias member 48 can be configured to bias the inner tube 20 in a distal direction along the longitudinal axis A so as to help maintain the inner tube's teeth 26 in operative engagement with the first jaw's teeth 34. A proximal end of the outer tube bias member 50 can abut the anchor member 42, and the outer tube bias member 50 can be configured to bias the outer tube member 22 in a distal direction along the longitudinal axis A so as to help maintain the outer tube's teeth 28 in operative engagement with the second jaw's teeth 36.

The surgical device 2 can include a movement assembly configured to facilitate rotation of the inner and outer tubes 20, 22 in response to selective actuation of the first actuator 14a, 14b and the second actuator 16. The movement assembly can be operatively connected to both the first actuator 14a, 14b and the second actuator 16 to provide for the selected actuation, e.g., the jaw opening/closing via the first actuator 14a, 14b or the jaw articulation via the second actuator 16. As shown in FIGS. 3-5, 8, and 9, the movement assembly can include a first helical gear 44, a second helical gear 46, a drive bushing 52, and an articulation sleeve 60. The first helical gear 44 and the second helical gear 46 can be axially aligned with the shaft's longitudinal axis A. The first and second helical gears 44, 46 can be disposed within the drive bushing 52. The drive bushing 52 can be disposed at least partially within the articulation sleeve 60. The first helical gear 44, the second helical gear 46, the drive bushing 52, and the articulation sleeve 60 can all be coaxially aligned, as in this illustrated embodiment.

The first helical gear 44, also referred to herein as a first "drum," can have a variety of sizes, shapes, and configurations. In an exemplary embodiment, the first helical gear 44 can be rigid and can be cannulated. The first helical gear 44 can be fixedly attached to the inner tube 20, such as by a proximal end of the inner tube 20 being fixedly attached to the first helical gear 44, e.g., via welding, adhesive, etc. In this way, rotation of the first helical gear 44 can cause the inner tube 20 to rotate in the same direction as the first helical gear 44. The first helical gear 44 can be longitudinally fixed relative to the inner tube 20 and to the housing 38. The first helical gear 44 can have a first thread 45 formed in an exterior surface thereof. The first thread 45 can, as in this illustrated embodiment, include a plurality of discrete threads. The first thread 45 can be configured as a groove formed in the first drum's exterior surface. The first thread 45 is right-handed in this illustrated embodiment, but in another embodiment, the first thread 45 can be left-handed.

The second helical gear 46, also referred to herein as a second "drum," can have a variety of sizes, shapes, and configurations. The second helical gear 46 can generally be configured similar to the first helical gear 44. In an exemplary embodiment, the second helical gear 46 can be rigid and can be cannulated. The second helical gear 46 can be fixedly attached to the outer tube 22, such as by a proximal end of the outer tube 22 being fixedly attached to the second helical gear 46, e.g., via welding, adhesive, etc. In this way, rotation of the second helical gear 46 can cause the outer tube 22 to rotate in the same direction as the second helical gear 46. The second helical gear 46 can be longitudinally fixed relative to the outer tube 22 and to the housing 38. The second helical gear 46 can be located distal to the first helical gear 44 along the shaft's longitudinal axis A. In another embodiment, the first helical gear 44 can be located distal to the second helical gear 46. A proximal face of the second helical gear 46 can abut a distal face of the first helical gear 44, as in this illustrated embodiment, as shown in FIG. 3. The second helical gear 46 can have a second thread 47 formed in an exterior surface thereof. The second thread 47 can, as in this illustrated embodiment, include a plurality of discrete threads. The second thread 47 can be configured as a groove formed in the second drum's exterior surface. The first and second threads 45, 47 can spiral in opposite direction from one another, e.g., the first thread 45 being right-handed and the second thread 47 being left-handed. The opposite spiraling of the first and second threads 45, 47 can facilitate independent rotation of the inner and outer tubes 20, 22 as discussed further below.

The drive bushing 52 can have a variety of sizes, shapes, and configurations. In an exemplary embodiment, the drive bushing 52 can be rigid. As shown in FIGS. 3-5, 8, and 9, the drive bushing 52 can be have the first and second helical gears 44, 46 disposed within an inner lumen thereof. The drive bushing 52 can be coaxial with the first and second helical gears 44, 46, as in this illustrated embodiment. The drive bushing 52 is shown in FIG. 4 in an exploded view as two halves similar to the housing halves 38a, 38b, however the drive bushing 52 can be a single piece or can be more than two pieces attached together. The drive bushing 52 can include at least two pins that each extend radially inward, e.g., extend radially inward from an interior surface of the drive bushing 52. At least one of the pins can be seated in the thread 45 of the first helical gear 44, and at least one other of the pins can be seated in the thread 47 of the second helical gear 46. In this illustrated embodiment, the bushing 52 includes four pins, two engaged with the first thread 45 and two engaged with the second thread 47. Only first and second ones of the pins 52a, 52b are visible in FIG. 4, and a fourth pin 52c is visible in FIG. 8. A third one of the pins is obscured but is similar to the illustrated first, second, and third pins 52a, 52b, 52c. The first pin 52a and the third pin can be engaged with the first thread 45. The second pin 52b and the fourth pin 52c can be engaged with the second thread 47.

The first actuator 14a, 14b can be operatively connected to the drive bushing 52. The drive bushing 52 can have pivot connections 51a, 51b on opposite sides thereof. The pivot connections 51a, 51b can allow for the arms 14a, 14b to be pivotally connected to the drive bushing 52. As the arms 14a, 14b are moved toward and away from the main housing 38, the pivot connections 51a, 51b can facilitate rotation of the drive bushing 52 about the longitudinal axis A, as discussed further below.

Figure 9:
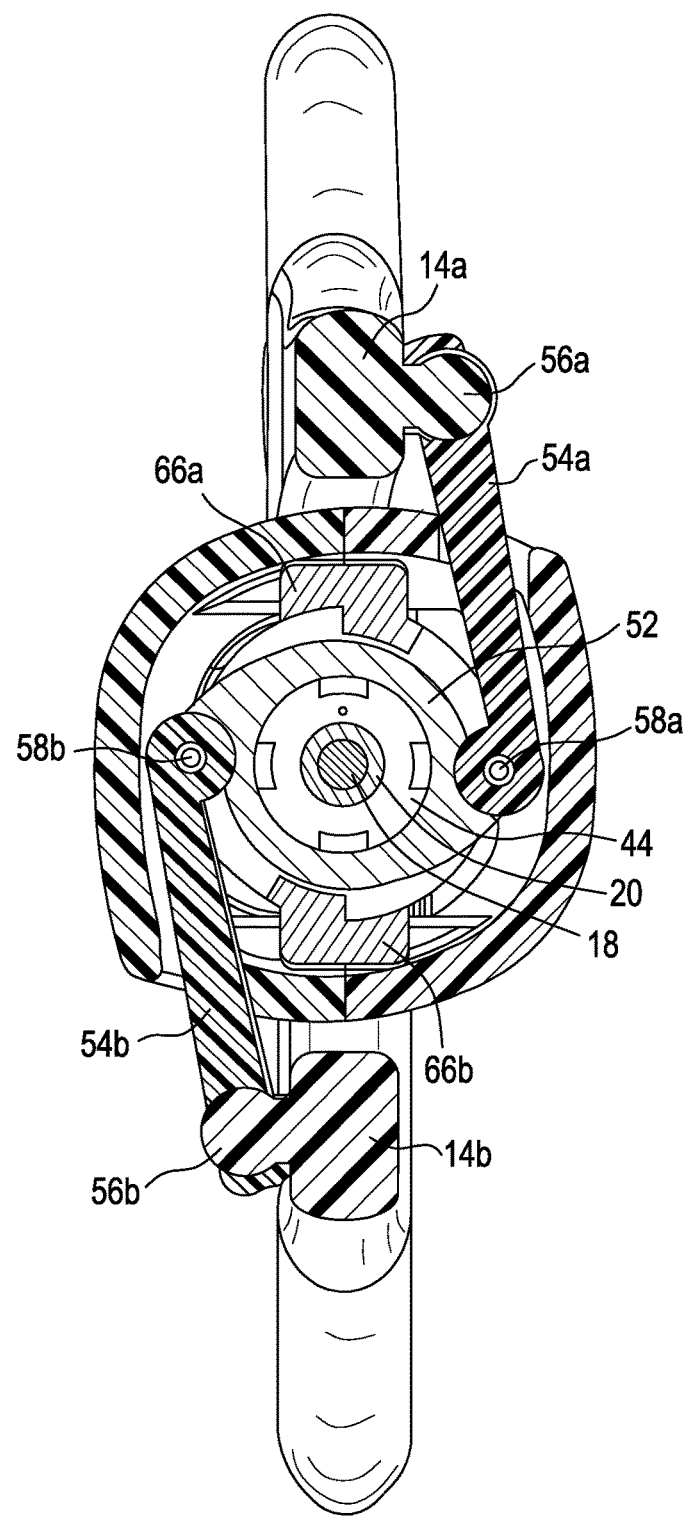
FIG. 9 is another cross-sectional view of the surgical device of FIG. 3.

The arms 14a, 14b can be pivoted by a user, e.g., moved toward and away from the housing 38, so as to open and close the jaws 12a, 12b of the end effector 8. As shown in FIGS. 2, 5, and 9, the arms 14a, 14b each can have a drive link 54a, 54b pivotally attached thereto at an intermediate location of the arms 14a, 14b between proximal and distal ends thereof. Each of the drive links 54a, 54b can include a hole configured to movably attach to a ball joint 56a, 56b, respectfully, of each handle 14a, 14b, as shown in FIGS. 5 and 9. At an opposite end of the drive link 54a, 54b from the holes attached to the ball joints 56a, 56b, the drive links 54a, 54b can be pivotally attached to the drive bushing 52 at the first and second pivot connections 51a, 51b, respectively. The first and second drive links 54a, 54b can be pivotally attached to the pivot connections 51a, 51b via first and second pins 58a, 58b, respectively. This coupling of the arms 14a, 14b to the drive bushing 52 via the drive links 54a, 54b, can allow for the drive bushing 52 to rotate about the longitudinal axis A in response to the drive arms 14a, 14b being actuated, e.g., moved toward or away from the main housing 38, as discussed further below.

The articulation sleeve 60 can have a variety of sizes, shapes, and configurations. The articulation sleeve 60 can be rigid. The articulation sleeve 60 can have an interior cavity in which first helical gear 44, the second helical gear 46, and the drive bushing 52 can be disposed, as shown in FIG. 4. The bushing 52 can be disposed within the sleeve 60 at a fixed longitudinal position relative thereto, as shown in FIG. 3 in which a proximal face of the bushing 52 abuts a distal face of the sleeve 60 and a distal face of the bushing 52 abuts a proximal face of the sleeve 60. The articulation sleeve 60 can be coaxially aligned with the outer tube spring 50, the drive bushing 52, and the shaft 6. The articulation sleeve 60 can include multiple pieces, e.g., two halves, or the articulation sleeve 60 can be a single piece, similar to the housing 38 that can be one or more pieces. In this illustrated embodiment, the articulation sleeve 60 is a single piece.

The articulation sleeve 60 can include at least one opening 61a, 61b therein that extends through a sidewall thereof. The at least one opening 61a, 61b can be configured to have the pivot connections 51a, 51b of the drive bushing 52 exposed and/or extending therethrough, which can allow the drive links 54a, 54b to be attached to the drive bushing 52 with the drive bushing 52 seated within the sleeve 60. Upper and lower edges of the at least one opening 61a, 61b can be configured to limit the rotation of the drive bushing 52 relative to the articulation sleeve 60, as the pivot connections 51a, 51b can abut the upper and lower edges, depending on a direction of the bushing's rotation, so as to stop the bushing's rotation. The opening's upper and lower edges can thus be configured to limit the bushing's rotation past upper and lower vertical limits of the at least one opening 61a, 61b. The at least one opening 61a, 61b can be located in a proximal portion of the sleeve 60.

The proximal portion of the articulation sleeve 60 can include at least one guide rail 66a, 66b configured to facilitate longitudinal movement of the sleeve 60 relative to the housing 38. In this illustrated embodiment, the sleeve 60 includes two guide rails 66a, 66b, one on a top surface thereof and the other on a bottom surface thereof, but the sleeve 60 can include any number of guide rails in these and/or other locations. The guide rails 66a, 66b can be configured to slide within corresponding guide tracks 67a, 67b formed in in the main housing 38. The tracks 67a, 67b and the rails 66a, 66b can cooperate to limit longitudinal movement of the sleeve 60 proximally and distally, e.g., to constrain movement of the articulation sleeve 60 along the longitudinal axis A. The tracks 67a, 67b and the rails 66a, 66b can also cooperate to help smoothly longitudinally move the sleeve 60 proximally and distally. The first and second guides 66a, 66b can be located along at least a length of the at least one opening 61a, 61b, as in this illustrated embodiment. In another embodiment, the housing 38 can include one or more guide rails, and the sleeve 60 can include one or more corresponding guide tracks.

A distal portion of the articulation sleeve 60 can include at least one thread 68 formed in an outer surface thereof. The at least one thread 68 of the sleeve 60 can include a groove formed in the sleeve's exterior surface. The sleeve thread 68 is left-handed in this illustrated embodiment, but in another embodiment, the sleeve thread 68 can be right-handed. A direction of the sleeve thread 68 can dictate whether the end effector 8 articulates up or down relative to the longitudinal axis A in response to actuation of the second actuator 16, as discussed further below.

The drive bushing 52 can be configured to rotate about the longitudinal axis A, relative to the actuation sleeve 60, in response to actuation of the first actuator 14a, 14b. The first pin 52a and the third pin can be engaged with the first thread 45 of the first helical gear 44, e.g., the first pin 52a and the third pin can be seated within the groove formed in the first drum's exterior surface, and the second pin 52b and fourth pin 52c can be engaged with the second thread 47 of the second helical gear 46, e.g., the second pin 52b and the fourth pin 52c can be seated within the groove formed in the second drum's exterior surface. As the bushing 52 rotates, the pins can push their respective helical gears 44, 46, e.g., by the pins pushing against sidewalls of the thread 45, 47 in which they are seated. The rotation of the bushing 52 can thus cause the helical gears 44, 46 to be rotated in a same direction as the drive bushing 52, e.g., both clockwise or both counterclockwise. The helical gears 44, 46 can remain in a longitudinally fixed position during this rotation. The sleeve 60 can remain fixed longitudinally and rotationally when the bushing 52 and the gears 44, 46 rotate. As mentioned above, the first and second helical gears 44, 46 can be operatively connected to the inner and outer tubes 20, 22 such that the rotation of the helical gears 44, 46 can cause their connected one of the tubes 20, 22 to also rotate. In other words, as the first and second helical gears 44, 46 rotate in the same direction, they can drive the inner and outer tubes 20, 22, respectively, in the same direction. The rotation of the inner tube 20 can cause the first jaw 12a to pivot at the joint 10 in a first direction, and the rotation of the outer tube 22 in the same direction as the inner tube 20 can cause the second jaw 12b to pivot in a second direction that is opposite to the first direction. Thus, when the inner and outer tubes 20, 22 rotate in a same direction as one another, the jaws 12a, 12b can pivot in opposite directions from one another. When the jaws 12a, 12b pivot in opposite directions, the movement either opens or closes the jaws 12a, 12b depending on whether the jaws 12a, 12b are moving toward one another (jaws closing) or away from one another (jaws opening). Whether the jaws 12a, 12b open or close can depend on whether the handles 14a, 14b are being moved toward the housing 38 (jaws closing) or away from the housing 38 (jaws opening).

The articulation sleeve 60 can be configured to move in response to actuation of the second actuator 16. The at least one pin 74 of the knob 16 can be seated within the groove formed in the sleeve's outer surface. When the second actuator 16 is actuated, e.g., when the articulation knob 16 is rotated, the at least one pin 74 of the knob 16 can slide within the at least one slot 72. Because the knob 16 can be in a fixed longitudinal position by being seated within the recess 68, the movement of the at least one pin 74 seated within the sleeve thread 68 can cause the sleeve 60 to move longitudinally in response to rotation of the knob 16.

The longitudinal movement of the sleeve 60 can cause the drive bushing 52 seated therein to also move longitudinally. The bushing 52 being at a fixed longitudinal position relative to the sleeve 60, as mentioned above, can allow for the sleeve's longitudinal movement to cause longitudinal movement of the bushing 52. As the drive bushing 52 moves longitudinally, the second pin 52b and the fourth pin 52c engaged with the second thread 47 of the second helical gear 46 can slide within the second thread 47 so as to rotate the second helical gear 46 in a first direction. Similarly, as the drive bushing 52 moves longitudinally, the first pin 52a and the third pin engaged with the first thread 45 of the first helical gear 44 can slide within the first thread 45 so as to rotate the first helical gear 44 in a second direction that is opposite to the first direction. The first and second helical gears 44, 46 can rotate in the opposing first and second directions due to the first and second threads 45, 47 of the first and second helical gears 44, 46 having opposite helical directions. The first and second directions can depend on whether the knob 16 is turned clockwise or counterclockwise. In this illustrated embodiment, the knob 16 rotating clockwise can cause the sleeve 60 to move in a distal direction, which can cause the outer tube 22 to rotate clockwise and the inner tube 20 to rotate counterclockwise, and the knob 16 rotating counterclockwise can cause the sleeve 60 to move in a proximal direction, which can cause the outer tube 22 to rotate counterclockwise and the inner tube 20 to rotate clockwise.

As the first helical gear 44 is rotated in the first direction, the first helical gear 44 can drive the inner tube 20 to rotate in the first direction. As the inner tube 20 is driven in the first direction, the inner tube 20 can cause the first jaw 12a to pivot at the joint 10. As the second helical gear 46 is rotated in the second direction, the second helical gear 46 can drive the outer tube 22 in the second direction. As the outer tube 22 is driven in the second direction, the outer tube 22 can drive the second jaw 12b to pivot at the joint 10 in a same direction as the first jaw 12a. The jaws 12a, 12b can thus articulate in response to actuation of the second actuator 16.

The surgical device 2 can be manipulated into various configurations as shown in embodiments illustrated in FIGS. 10-19. These different configurations can be achieved by manipulating the first actuator 14a, 14b and the second actuator 16 in a variety of different ways, as discussed further below. Although certain configurations are discussed with respect to FIGS. 10-19 as being "first," "second," etc., the configurations can be achieved in a different order depending on an order of a user's selected actuation of the first actuator 14a, 14b and second actuator 16. In some uses of the device 2, not all configurations will be achieved, such as if a user never needs to articulate the end effector 8 downward during use of the device 2 in a surgical procedure. For clarity of illustration, the drive bushing 52 is not shown in FIGS. 12, 14, 16, and 18.

Figure 10:
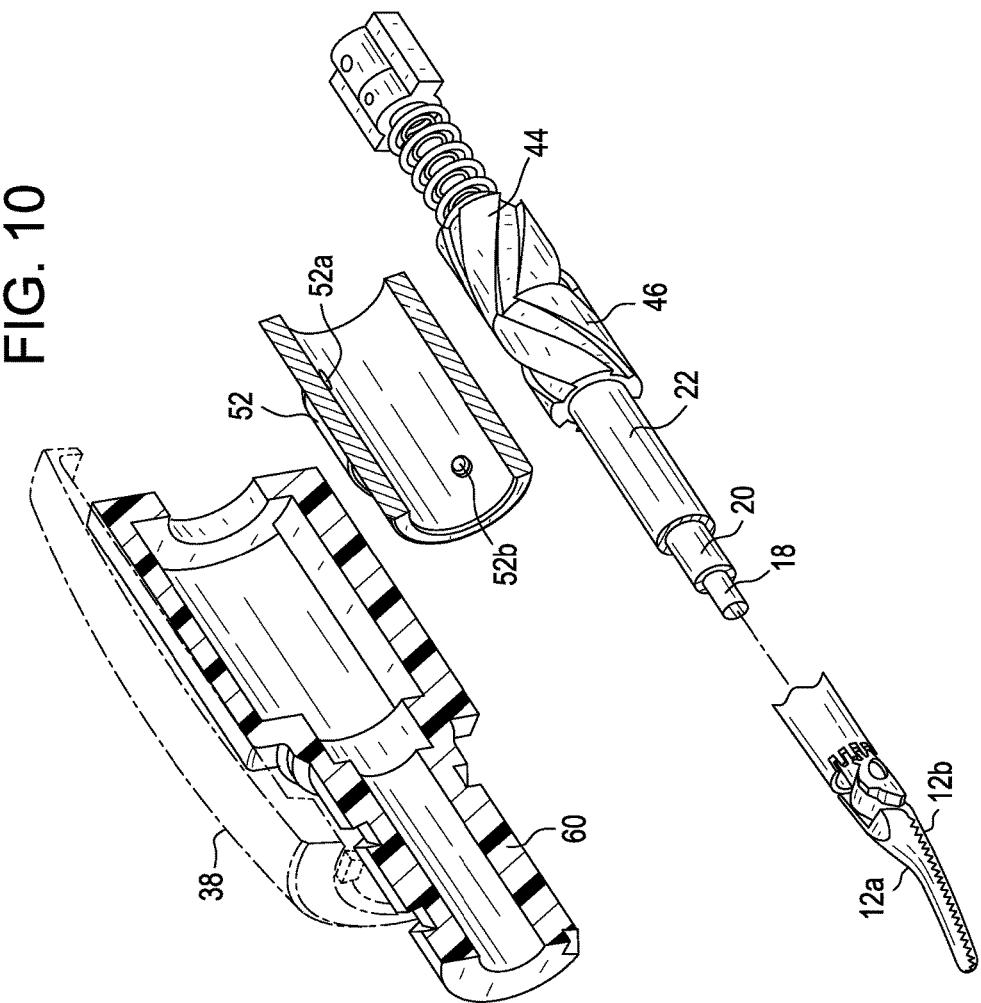
FIG. 10 is a partially exploded view of a portion of the surgical device of FIG. 1 with the surgical device in a first orientation.
Figure 11:
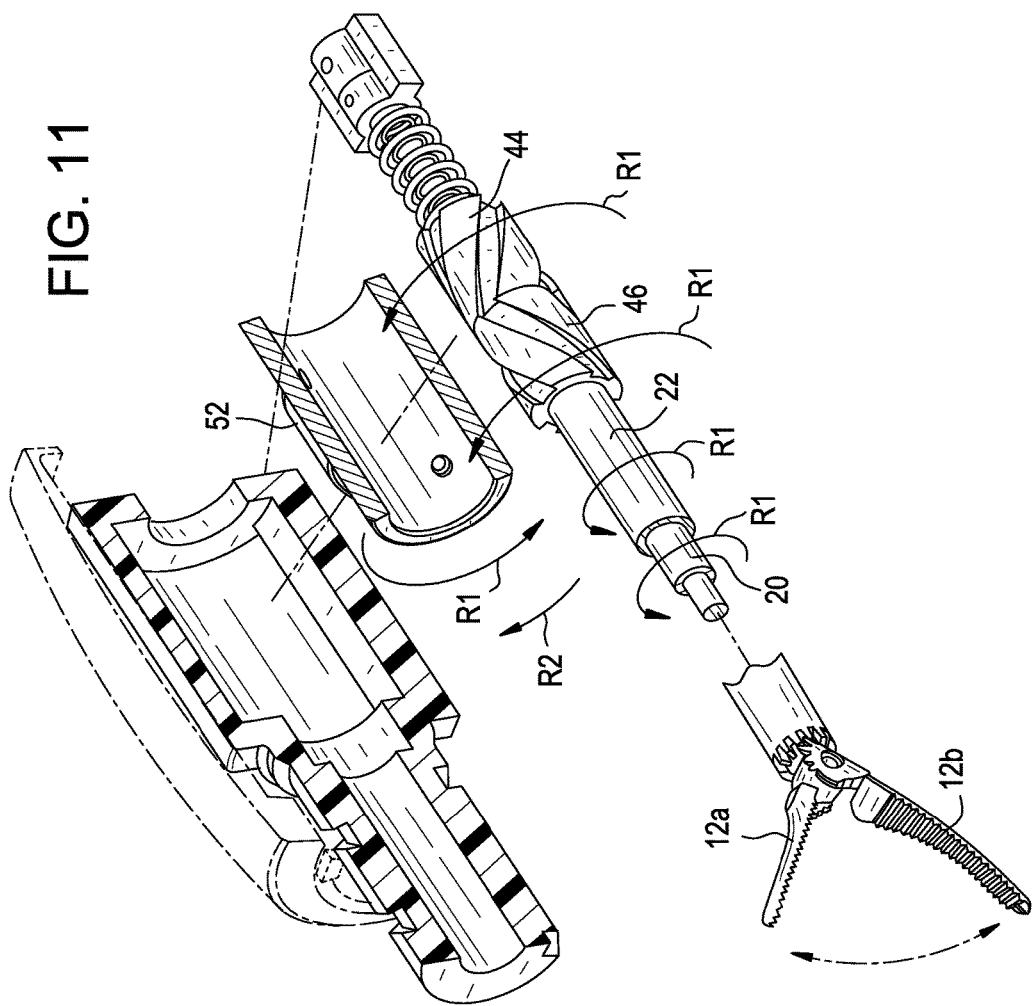
FIG. 11 is a partially exploded view of the surgical device of FIG. 10 in a second orientation moved from the first orientation.

FIG. 10, as well as FIGS. 1-3, show the device 2 in a first, default configuration in which the jaws 12a, 12b are closed and are not pivoted relative to the longitudinal axis A of the shaft 6, e.g., are non-articulated. As discussed above, the handles 14a, 14b can be pivoted toward the main housing 38, similar to movement of scissor handless. FIG. 11 shows movement of the device 2 from the first configuration to a second configuration in which the jaws 12a, 12b have moved from being closed to being open. As the arms 14a, 14b are pivoted at the handle pivot points 40a, 40b relative to the main housing 38, the drive links 54a, 54b transfer the movement of the arms 14a, 14b to rotation of the drive bushing 52. The drive links 54a, 54b can cause the drive bushing 52 to rotate about the shaft's longitudinal axis A. As the arms 14a, 14b are pivoted toward one another and toward the housing 18, the first drive link 54a moves up and the second drive link 54b moves down so as to cause the drive bushing 52 to rotate in a first direction R1, e.g., clockwise, which causes the first pin 52a and the third pin engaged in the first thread 45 of the first helical gear 44 to drive the first helical gear 44 to rotate in the first direction R1. As the first helical gear 44 rotates in the first direction R1, the inner tube 20 rotates in the first direction R1. Similarly, the drive bushing 52 rotating in the first direction R1 causes the second pin 52b and the fourth pin 52c engaged in the second thread 47 of the second helical gear 46, thereby driving the second helical gear 46 to rotate in the first direction R1, and hence the outer tube 22 to rotate in the first direction R1. The rotation of inner and outer tube 20, 22 in the same first direction R1 can drive teeth 34, 36 of the jaws 12a, 12b, respectfully, to rotate the jaws 12a, 12b away from one other so as to open the end effector 8, as shown in FIG. 11. The end effector 8 can be closed similar to that discussed above regarding the end effector 8 being opened. In general, the handles 14a, 14b can moved toward one another and toward the housing 38 so as to rotate the bushing 52 about the longitudinal axis A in a second direction R2, e.g., counterclockwise, thereby causing the first and second helical gears 44, 46, the inner tube 20, and the outer tube 22 to also rotate in the second direction R2 so as to cause the jaws 12a, 12b to move toward one another toward the closed position.

Figure 12:
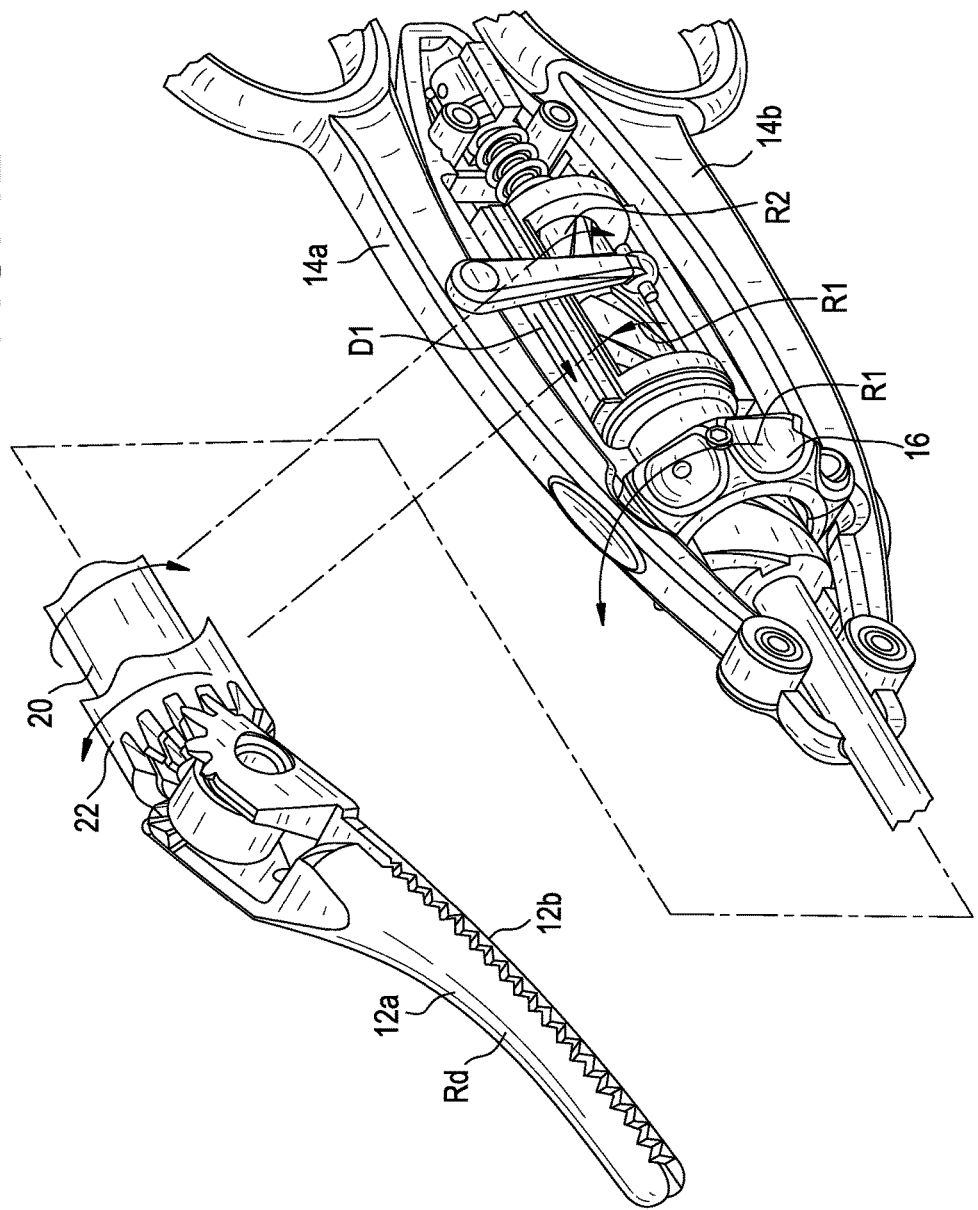
FIG. 12 is a partial cross-sectional view of the surgical device of FIG. 10 in a third orientation moved from the first orientation.
Figure 13:
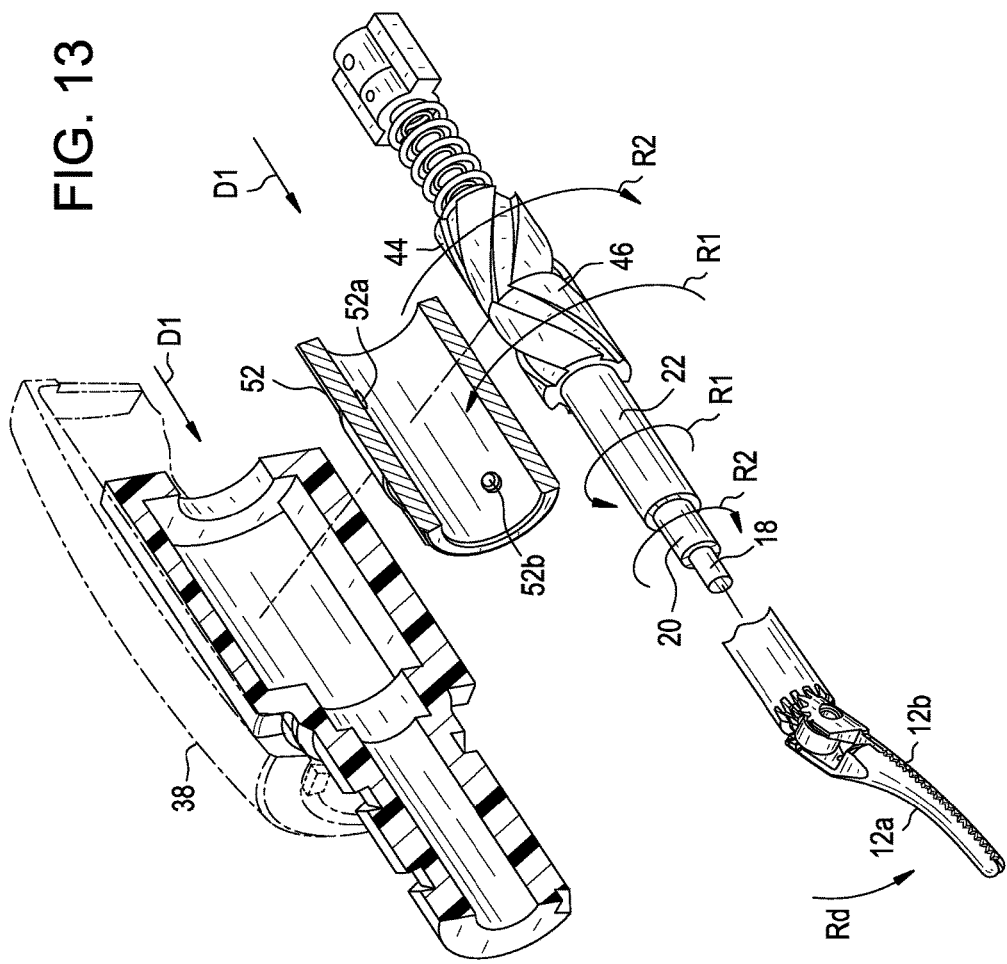
FIG. 13 is an exploded view of the surgical device of FIG. 12.

FIGS. 12 and 13 show the surgical device 2 moved to a third configuration from the first configuration of FIG. 10. In the third configuration, the jaws 12a, 12b are in a closed position and have been pivoted downward in a downward direction Rd relative to the longitudinal axis A of the shaft 6. The device 2 is described as moving from the first configuration to the third configuration for ease of discussion. The jaws 12a, 12b can be articulated downward with the jaws 12a, 12b open, closed, or at an intermediate position therebetween, and from one downward articulated position to another downward articulated position. The articulation knob 16 can be rotated in the first direction R1. As the articulation knob 16 rotates in the first direction R1 the pin 74a engaged in sleeve thread 68 can slide therein so as to drive the articulation sleeve 60 longitudinally in a first direction D1, e.g., a distal direction. Movement of the articulation sleeve 60 in the first direction D1 can move the articulation sleeve 60 from a proximal location to a more distal location as the articulation sleeve 60 moves distally relative to the main housing 38.

As the articulation sleeve 60 moves longitudinally in the first direction D1, the drive bushing 52 also moves longitudinally in the first direction D1. The second pin 52b and the fourth pin 52c can slide in the second thread 47 of the second helical gear 46, thereby driving the second helical gear 46 and the outer tube 22 in the first direction R1. Similar, the first pin 52a and the third pin can slide in the first thread 45 of the first helical gear 44, thereby driving the first helical gear 44 and the inner tube 20 in the second direction R2 opposite to the first direction R1 in which the second helical gear 46 is rotating. The rotation of the outer tube 22, and hence the teeth 28 at the distal end of the outer tube 22, movably engages the second teeth 36 of the second jaw 12b so as to articulate the second jaw 12b downward in the downward direction Rd. Similarly, the rotation of the inner tube 20, and hence the teeth 26 at the distal end of the inner tube 20, movably engages the first teeth 34 of the first jaw 12a so as to articulate the first jaw 12a downward in the downward direction Rd. Therefore, both of the jaws 12a, 12b can be driven in the same downward direction Rd relative to the shaft 6 in response to rotation of the knob 16 in the first direction R1. If the jaws 12a, 12b were not closed prior to the downward pivoting, the jaws 12a, 12b can be closed by the actuation of the arms 14a, 14b after the downward pivoting actuation.

Figure 14:
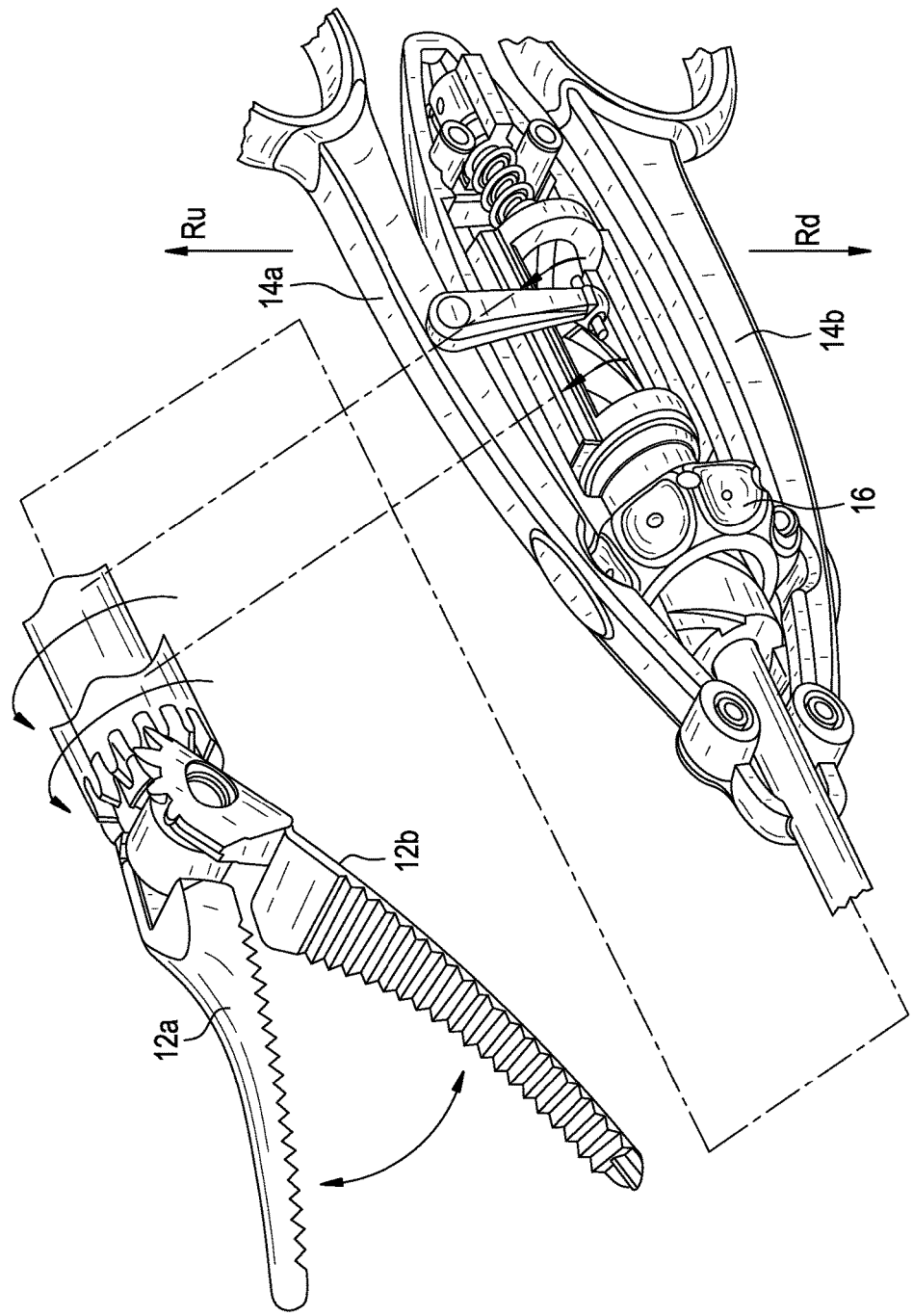
FIG. 14 is a partial cross-sectional view of the surgical device of FIG. 12 in a fourth orientation moved from the third orientation.
Figure 15:
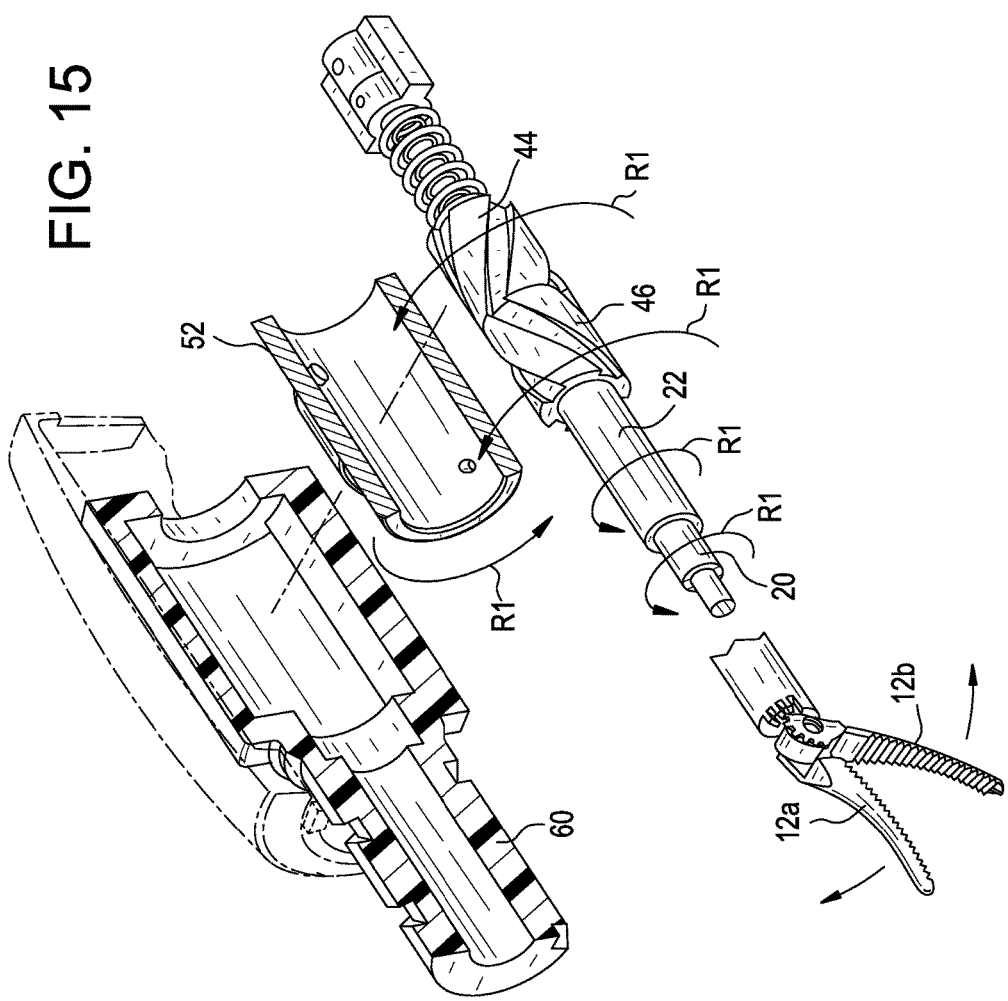
FIG. 15 is an exploded view of the surgical device of FIG. 14.

FIGS. 14 and 15 show the device 2 moved to a fourth configuration from the third configuration of FIGS. 12 and 13. In the fourth configuration, the jaws 12a, 12b are opened when the jaws 12a, 12b are in the articulated downward position. As mentioned above, the jaws 12a, 12b can alternatively be opened before being pivoted downward. The jaws 12a, 12b can be opened similar to that discussed with regards to FIG. 11, with the handles 14a, 14b being moved apart from one another in opposed upward and downward directions Ru, Rd.

Figure 16:
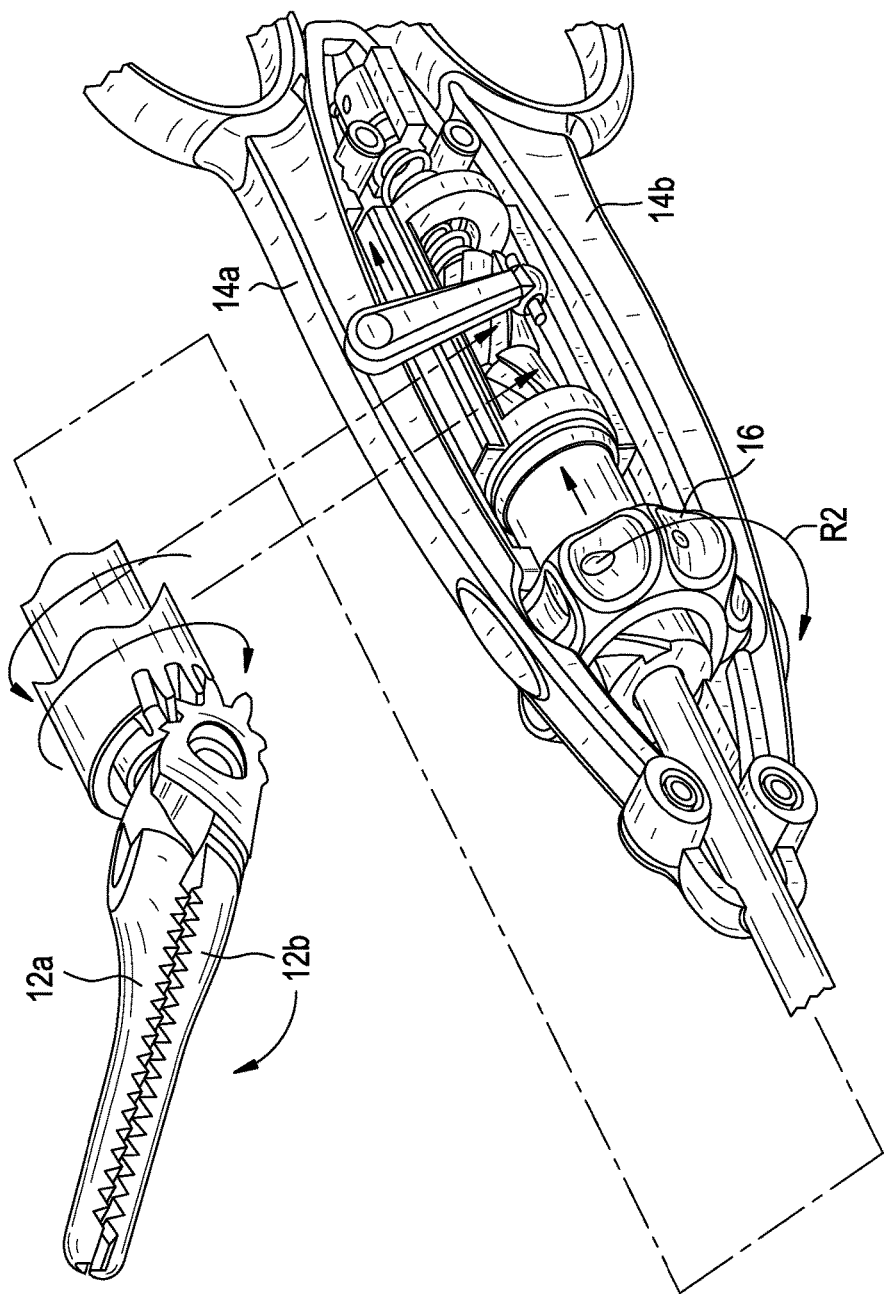
FIG. 16 is a partial cross-sectional view of the surgical device of FIG. 10 in a fifth orientation moved from the first orientation.
Figure 17:
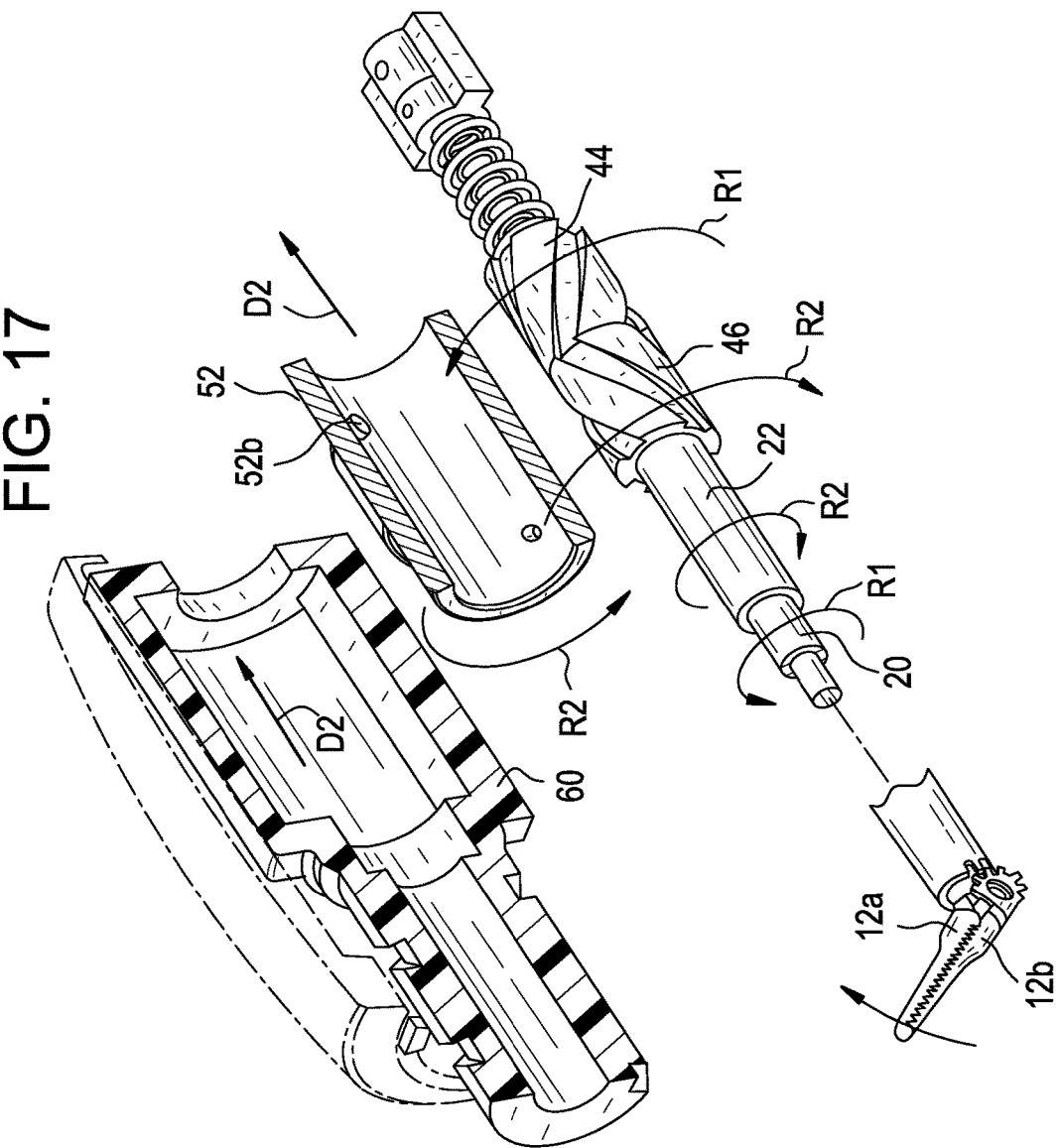
FIG. 17 is an exploded view of the surgical device of FIG. 16.

FIGS. 16 and 17 show the surgical device 2 moved to a fifth position from the first configuration of FIG. 10. In the fifth configuration, the jaws 12a, 12b are in a closed position and have been pivoted upward in an upward direction Ru relative to the longitudinal axis A of the shaft 6. The device 2 is described as moving from the first configuration to the fifth configuration for ease of discussion. The jaws 12a, 12b can be articulated upward with the jaws 12a, 12b open, closed, or at an intermediate position therebetween, and from one upward articulated position to another upward articulated position. Articulating the jaws 12a, 12b upward can be achieved similar to that discussed above with respect to the jaws 12, 12b being articulated downward, except that the knob 12 can be rotated in the second direction R2. The rotation of the knob 16 in the second direction R2 can cause the sleeve 60 and the bushing 52 to move in a second direction D2, e.g., a proximal direction, thereby causing the helical gears 44, 46 to rotate in opposite directions R1, R2. The inner and outer tubes 20, 22 thus rotate in opposite directions, causing the jaws 12a, 12b to articulate upward. Actuation of the articulation sleeve 60 in the second direction D2 can move the articulation sleeve 60 from a distal location to a more proximal location as the articulation sleeve 60 moves proximally longitudinally relative to the main housing 38.

Figure 18:
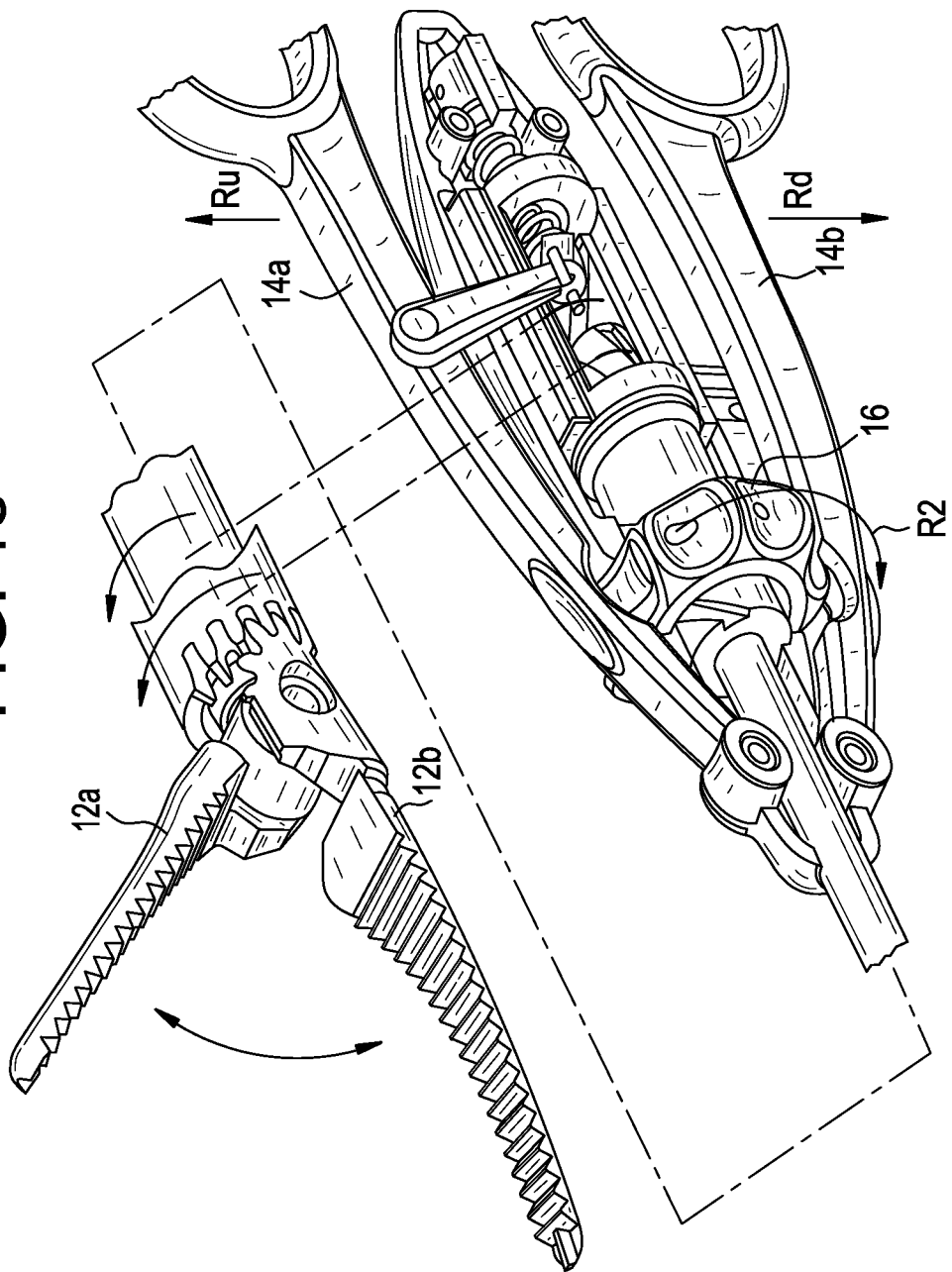
FIG. 18 is a partial cross-sectional view of the surgical device of FIG. 10 in a sixth orientation moved from the first orientation.
Figure 19:
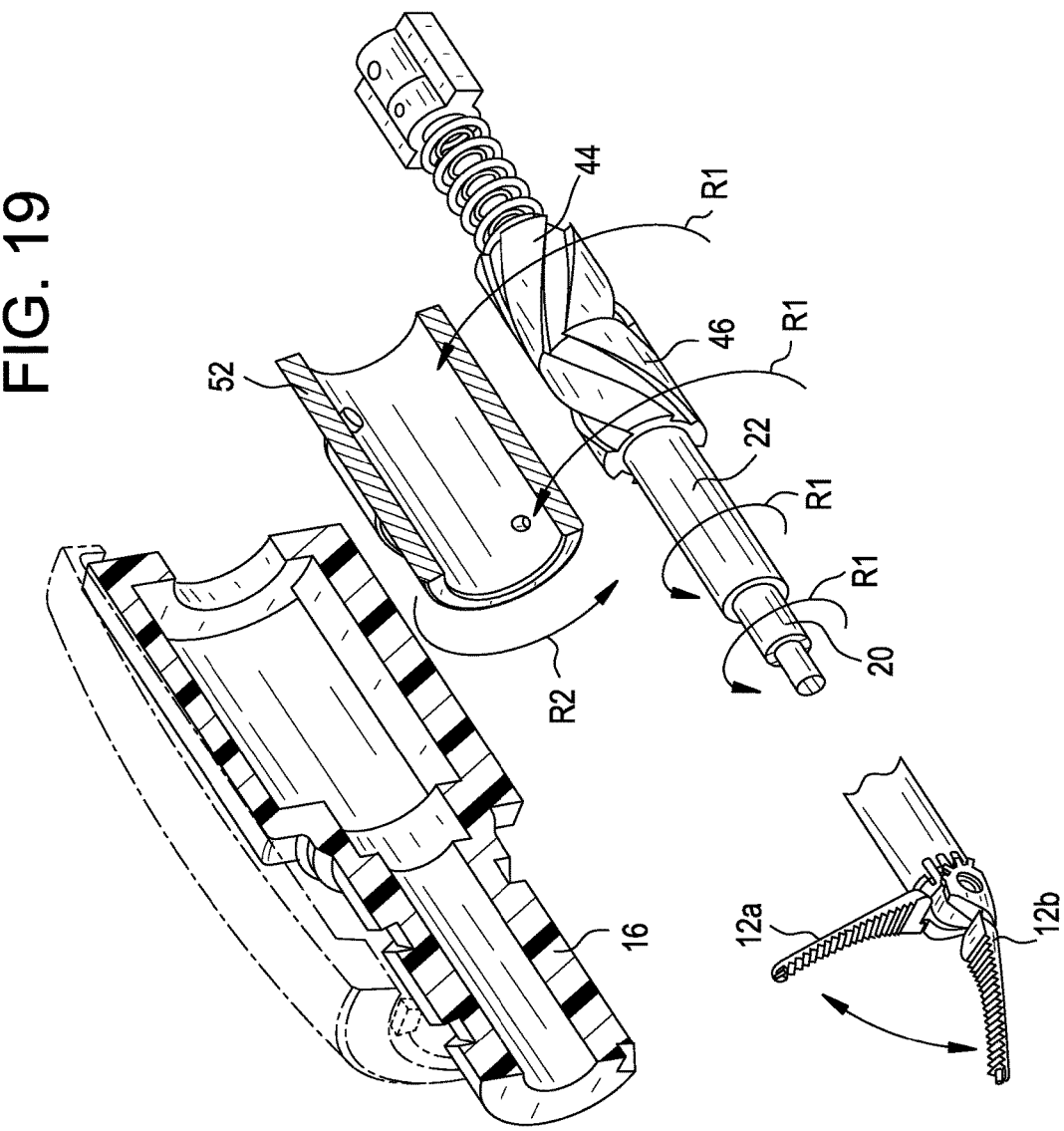
FIG. 19 is an exploded view of the surgical device of FIG. 18.

FIGS. 18 and 19 show the device 2 moved to a sixth configuration from the fifth configuration of FIGS. 16 and 17. In the sixth configuration, the jaws 12a, 12b are opened when the jaws 12a, 12b are in the articulated upward position. As mentioned above, the jaws 12a, 12b can alternatively be opened before being pivoted upward. The jaws 12a, 12b can be opened similar to that discussed with regards to FIG. 11, with the handles 14a, 14b being moved apart from one another in opposed upward and downward directions Ru, Rd.

The surgical device 2 in the embodiment of FIG. 1 is non-powered such that the device's jaw articulation and jaw opening/closing can be achieved mechanically without using any electrical power. In other embodiments, a surgical device can be powered such that electrical power is used for at least one of jaw articulation and jaw opening/closing. In an exemplary embodiment, a surgical device can be powered for jaw articulation and can be non-powered for jaw opening/closing. Jaw opening/closing can be more precisely controlled by a user of the device when performed mechanically, since the user can palpably feel the opening and the closing, which can provide an indication as to type, size, etc. of tissue being clamped by the jaws, thereby providing overall good user experience. Articulation not involving user feel need not detract from overall good user experience since articulation is more directed to device positioned than to tissue manipulation.

FIGS. 20-23 illustrate one embodiment of a powered surgical device 102. The surgical device 102 can generally be configured and used similar to the surgical device 2 of FIG. 1. The device 102 can include a proximal handle portion 104, an end effector 108 including first and second jaws 112a, 112b, an elongate shaft 106, a pivot joint 110, a pin 111 vat the pivot joint 110, a movement assembly, a first actuator 114a, 114b, a second actuator 116, first and second drive links 154a, 154b, an inner tube bias member 148, and outer tube bias member 150, an anchor member 142, one or more anchor pins 142a, 142b, and a main housing 138 including housing halves 138a, 138b. The elongate shaft 106 can include a central shaft 118, an inner tube 120, and an outer tube 120. The movement assembly can include a first helical gear 144, a second helical gear 146, a drive bushing 152, and an articulation sleeve 160.

The first actuator 114a, 114b can be configured to effect the opening and closing of the opposed jaws 112a, 112b, e.g., movement of the jaws 112a, 112b toward and away from one another, similar to that discussed above regarding the first actuator 14a, 14b of FIG. 1.

The second actuator 116 can be configured to effect the articulation of the opposed jaws 112a, 112b, e.g., movement of both jaws 112a, 112b in a same direction relative to the shaft's longitudinal axis A', similar to the articulation movement discussed above with respect to the jaws 12a, 12b of FIG. 1, but the articulation for the device 102 of FIG. 20 can be achieved using electrical power. The device 2 can include a power source (not shown), a motor 121, a first transmission gear 124, a second transmission 126, and a drive shaft 128 that can be configured to assist with powered articulation. The power source, the motor 121, the first transmission gear 124, the second transmission 126, and the drive shaft 128 can be housed within the main housing 138. In general, actuation of the second actuator 116 can cause the motor 121 to provide power that longitudinally moves the articulation sleeve 160 and the bushing 152, similar to that discussed above for the articulation sleeve 60 and the bushing 152 of the device 2 of FIG. 1, so as to articulate the end effector 108.

The motor 121 can have a variety of configurations e.g., a rotary motor, an electric motor, a pneumatic motor, etc.

Figure 23:
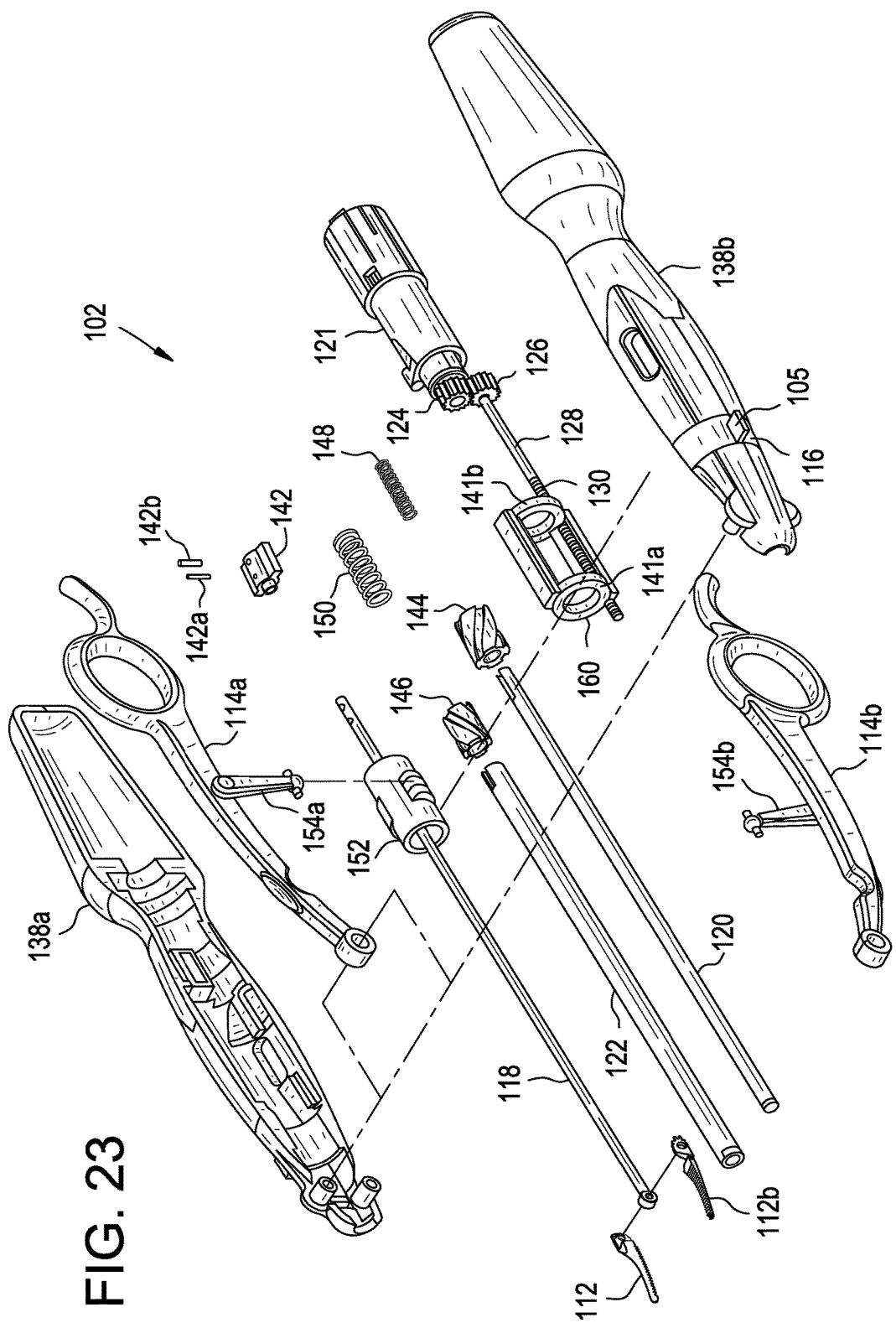
FIG. 23 is an exploded view of the surgical device of FIG. 20.

The motor 121 can be configured to be powered by the power source. The power source can have a variety of configurations, e.g., a battery, an electrical power cord, a pneumatic source, etc. The power source can be disposed within the housing 138, as in this illustrated embodiment, or the power source can be external, such as if the power source includes an electrical power cord extending from the housing 138 and configured to be plugged into a generator, a wall outlet, etc. Similarly, the motor 121 is disposed within the housing 138 in this illustrated embodiment, but the motor can be located outside the housing 138. The motor 121 can be configured to be triggered on via actuation of the second actuator 116. The motor 121 can be operatively connected to the first transmission gear 124. The motor 121 can be coaxially aligned with the first transmission gear 124 so that upon power being provided to the motor 121 from the power source, the first transmission gear 124 can be configured rotate either clockwise or counterclockwise, depending on the actuation of the second actuator 116. The first transmission gear 124 can be operatively connected to the second transmission gear 126, as shown in FIGS. 21-23. The second transmission gear 126 can have the drive shaft 128 operatively connected thereto such that rotation of the second transmission gear 126 can drive rotation of the drive shaft 128. The drive shaft 128 can have threads 130 at a distal portion thereof. The drive shaft 128 can have the articulation sleeve 160 operatively attached thereto via the threads 130 such that upon rotation of the drive shaft 128, the articulation sleeve 160 can be moved longitudinally, either distally or proximally depending on whether the drive shaft 128 is rotating clockwise or counterclockwise. The electrical power provided by the motor 121 can thus be translated into mechanical movement of the articulation sleeve 160, and hence mechanical movement of the bushing 152, the inner and outer tubes 120, 122, and the first and second jaws 112a, 112b. The articulation sleeve 160 can include at least one threaded member 141a, 141b configured to threadably engage the drive shaft threads 130.

The second actuator 116 can have a variety of sizes, shapes, and configurations. In an exemplary embodiment, the second actuator 116 can include at least one tab 105 configured to be manually actuated by a user, e.g., by being pushed clockwise C1 or counterclockwise C2. Only one tab 105 is visible in FIGS. 20 and 23. A second tab is located on the other housing half 138 but is obscured in FIGS. 20 and 23. Having two tabs 105 on either side of the housing 138 can facilitate actuation of the second actuator 116 regardless of whether a left hand or a right hand of a user is holding the device 2. Actuation of the second actuator 116 can cause a switch to be closed, thereby triggering the motor to turn on. For example, movement of the at least one tab 105 clockwise C1 can cause a first circuit to close, thereby causing the motor 121 to turn on and rotate the first transmission gear 124 clockwise so as to articulate the end effector 8, and movement of the at least one tab 105 counterclockwise C2 can cause a second circuit to close, thereby causing the motor 121 to turn on and rotate the first transmission gear 124 counterclockwise so as to articulate the end effector 8. When the at least one tab 105 is released, the closed first or second circuit can open, thereby causing the motor 121 to turn off and hence causing articulation of the end effector 8 to stop. The at least one tab 105 can be in wired communication with the first and second circuits and/or the motor 121, or the at least one tab 105 can be in wireless communication with the first and second circuits and/or the motor 121.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   advancing jaws at a distal end of a surgical instrument into a body, the surgical instrument including a handle, an outer tube extending distally from the handle, and an inner tube disposed within the outer tube and extending distally from the handle;
   actuating a first actuator coupled to the handle so as to cause the inner and outer tubes to rotate in opposite directions, thereby causing the jaws to articulate in a same direction as one another; and
   actuating a second actuator coupled to the handle so as to cause the inner and outer tubes to rotate in a same direction, thereby causing the jaws to selectively open and close.

2. The method of claim 1, wherein actuating the first actuator comprises rotating the first actuator in a first direction or in a second direction that is opposite to the first direction, the rotation of the first actuator in the first direction causing the outer tube to rotate in the first direction and causing the inner tube to rotate in the second direction, and the rotation of the first actuator in the second direction causing the outer tube to rotate in the second direction and causing the inner tube to rotate in the first direction.

3. The method of claim 1, wherein actuating the first actuator causes a motor to drive the rotation of the inner and outer tube in the opposite directions.

4. The method of claim 1, wherein the second actuator includes first and second handles, and actuating the second actuator comprises moving the first and second handles toward and away from one another.

* * * * *